United States Patent
Webb et al.

(10) Patent No.: US 10,737,102 B2
(45) Date of Patent: Aug. 11, 2020

(54) LEADLESS IMPLANTABLE DEVICE WITH DETACHABLE FIXATION

(71) Applicant: CARDIAC PACEMAKERS, INC., St. Paul, MN (US)

(72) Inventors: Erin Kristen Webb, Minneapolis, MN (US); Bryan J. Swackhamer, Shoreview, MN (US); Dana Sachs, Pine City, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 171 days.

(21) Appl. No.: 15/881,466

(22) Filed: Jan. 26, 2018

(65) Prior Publication Data

US 2018/0207434 A1 Jul. 26, 2018

Related U.S. Application Data

(60) Provisional application No. 62/450,865, filed on Jan. 26, 2017.

(51) Int. Cl.
*A61N 1/37* (2006.01)
*A61N 1/375* (2006.01)
(Continued)

(52) U.S. Cl.
CPC ......... *A61N 1/37518* (2017.08); *A61N 1/365* (2013.01); *A61N 1/3756* (2013.01);
(Continued)

(58) Field of Classification Search
USPC .......................................................... 607/9
See application file for complete search history.

(56) References Cited

U.S. PATENT DOCUMENTS 3,835,864 A   9/1974 Rasor et al.
3,943,936 A   3/1976 Rasor et al.
(Continued)

FOREIGN PATENT DOCUMENTS

AU   2008279789 B2   10/2011
AU   2008329620 B2   5/2014
(Continued)

OTHER PUBLICATIONS

US 8,886,318 B2, 11/2014, Jacobson et al. (withdrawn)
(Continued)

*Primary Examiner* — Nicole F Lavert
(74) *Attorney, Agent, or Firm* — Seager, Tuft & Wickhem LLP

(57) ABSTRACT

An implantable medical device (IMD) may include a fixation module, and a device module that is configured to be releasably connected to the fixation module. The device module may have a proximal end and a distal end, and may include a power source and a controller that is operably coupled to the power source. The controller may be configured to sense cardiac electrical activity via two or more electrodes and/or deliver pacing pulses via two or more electrodes. The device module may include a first part of a releasable connector while the fixation module may include a second part of the releasable connector, wherein the first part of the releasable connector and the second part of the releasable connector cooperate to releasably connect the device module with the fixation module.

19 Claims, 16 Drawing Sheets

(51) Int. Cl.
  *A61N 1/365* (2006.01)
  *A61N 1/05* (2006.01)
  *A61B 90/00* (2016.01)
  *A61N 1/372* (2006.01)

(52) U.S. Cl.
  CPC .. *A61N 1/37512* (2017.08); *A61B 2090/3966* (2016.02); *A61N 1/0573* (2013.01); *A61N 1/37205* (2013.01)

(56) References Cited

U.S. PATENT DOCUMENTS

| | | |
|---|---|---|
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Maas |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,537,200 A | 8/1985 | Widrow |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,887,609 A | 12/1989 | Cole |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,154,183 A | 10/1992 | Kreyenhagen et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,259,387 A | 11/1993 | DePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | deCoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,706,823 A | 1/1998 | Wodlinger |
| 5,709,215 A | 1/1998 | Perttu et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Rostami et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,935,078 A | 8/1999 | Feierbach |
| 5,941,906 A | 8/1999 | Barreras, Sr. et al. |
| 5,944,744 A | 8/1999 | Paul et al. |
| 5,954,757 A | 9/1999 | Gray |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | DePinto |
| 6,044,298 A | 3/2000 | Salo et al. |

(56) References Cited

U.S. PATENT DOCUMENTS

| | | |
|---|---|---|
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |

(56) References Cited

U.S. PATENT DOCUMENTS

| | | |
|---|---|---|
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,321,798 B2 | 1/2008 | Muhlenberg et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,418,298 B2 | 8/2008 | Shiroff et al. |
| 7,425,200 B2 | 9/2008 | Brockway et al. |
| 7,433,739 B1 | 10/2008 | Salys et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,546,166 B2 | 6/2009 | Michels et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,657,326 B2 | 2/2010 | Bodner et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,711,437 B1 | 5/2010 | Bornzin et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,751,905 B2 | 7/2010 | Feldmann et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,821 B1 | 12/2010 | Ryu et al. |
| 7,848,823 B2 | 12/2010 | Drasler et al. |
| 7,860,455 B2 | 12/2010 | Fukumoto et al. |
| 7,860,581 B2 | 12/2010 | Eckerdal et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,550 B1 | 3/2011 | Doan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,927 B2 | 4/2011 | Zarembo et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |

(56) References Cited

U.S. PATENT DOCUMENTS

| | | |
|---|---|---|
| 8,000,805 B2 | 8/2011 | Swoyer et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,036,756 B2 | 10/2011 | Swoyer et al. |
| 8,036,757 B2 | 10/2011 | Worley |
| 8,046,079 B2 | 10/2011 | Bange et al. |
| 8,046,080 B2 | 10/2011 | Von Arx et al. |
| 8,050,297 B2 | 11/2011 | DelMain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,090,451 B2 | 1/2012 | Tyson, Jr. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,262,578 B1 | 9/2012 | Bharmi et al. |
| 8,265,748 B2 | 9/2012 | Liu et al. |
| 8,265,757 B2 | 9/2012 | Mass et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |

(56) References Cited

U.S. PATENT DOCUMENTS

| | | |
|---|---|---|
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,868,186 B2 | 10/2014 | Kroll |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 * | 12/2015 | Boling ................ A61N 1/059 |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Régnier et al. |
| 9,457,193 B2 | 10/2016 | Klimovitch et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,522,276 B2 | 12/2016 | Shen et al. |
| 9,522,280 B2 | 12/2016 | Fishler et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,636,511 B2 | 5/2017 | Carney et al. |
| 9,669,223 B2 | 6/2017 | Auricchio et al. |
| 9,687,654 B2 | 6/2017 | Sheldon et al. |
| 9,687,655 B2 | 6/2017 | Pertijs et al. |
| 9,687,659 B2 | 6/2017 | Von Arx et al. |
| 9,694,186 B2 | 7/2017 | Carney et al. |
| 9,782,594 B2 | 10/2017 | Stahmann et al. |
| 9,782,601 B2 | 10/2017 | Ludwig |
| 9,789,317 B2 | 10/2017 | Greenhut et al. |
| 9,789,319 B2 | 10/2017 | Sambelashvili |
| 9,808,617 B2 | 11/2017 | Ostroff et al. |
| 9,808,628 B2 | 11/2017 | Sheldon et al. |
| 9,808,631 B2 | 11/2017 | Maile et al. |
| 9,808,632 B2 | 11/2017 | Reinke et al. |
| 9,808,633 B2 | 11/2017 | Bonner et al. |
| 9,808,637 B2 | 11/2017 | Sharma et al. |
| 9,855,414 B2 | 1/2018 | Marshall et al. |
| 9,855,430 B2 | 1/2018 | Ghosh et al. |
| 9,855,435 B2 | 1/2018 | Sahabi et al. |
| 9,861,815 B2 | 1/2018 | Tran et al. |
| 10,080,887 B2 | 9/2018 | Schmidt et al. |
| 10,080,888 B2 | 9/2018 | Kelly et al. |
| 10,080,900 B2 | 9/2018 | Ghosh et al. |
| 10,080,903 B2 | 9/2018 | Willis et al. |
| 10,086,206 B2 | 10/2018 | Sambelashvili |
| 10,118,026 B2 | 11/2018 | Grubac et al. |
| 10,124,163 B2 | 11/2018 | Ollivier et al. |
| 10,124,175 B2 | 11/2018 | Berthiaume et al. |
| 10,130,821 B2 | 11/2018 | Grubac et al. |
| 10,137,305 B2 | 11/2018 | Kane et al. |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |

(56) References Cited

U.S. PATENT DOCUMENTS

| | | |
|---|---|---|
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0230283 A1 | 11/2004 | Prinzen et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Von Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0294229 A1 | 11/2008 | Friedman et al. |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | M. |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0069983 A1 | 3/2010 | Peacock, III et al. |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |

(56) References Cited

U.S. PATENT DOCUMENTS

| | | |
|---|---|---|
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0298841 A1 | 11/2010 | Prinzen et al. |
| 2010/0312309 A1 | 12/2010 | Harding |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0270341 A1 | 11/2011 | Ruben et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Dal Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0245665 A1 | 9/2012 | Friedman et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0289776 A1 | 11/2012 | Keast et al. |
| 2012/0289815 A1 | 11/2012 | Keast et al. |
| 2012/0290021 A1 | 11/2012 | Saurkar et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2012/0330392 A1 | 12/2012 | Regnier et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0192611 A1 | 8/2013 | Taepke, II et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253309 A1 | 9/2013 | Allan et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |

(56) References Cited

U.S. PATENT DOCUMENTS

| | | |
|---|---|---|
| 2014/0074186 A1 | 3/2014 | Faltys et al. |
| 2014/0094891 A1 | 4/2014 | Pare et al. |
| 2014/0100624 A1 | 4/2014 | Ellingson |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222015 A1 | 8/2014 | Keast et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0343348 A1 | 11/2014 | Kaplan et al. |
| 2014/0371818 A1 | 12/2014 | Bond et al. |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0045868 A1 | 2/2015 | Bonner et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0126854 A1 | 5/2015 | Keast et al. |
| 2015/0157861 A1 | 6/2015 | Aghassian |
| 2015/0157866 A1 | 6/2015 | Demmer et al. |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0230699 A1 | 8/2015 | Berul et al. |
| 2015/0238769 A1 | 8/2015 | Demmer et al. |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306401 A1 | 10/2015 | Demmer et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2015/0335884 A1 | 11/2015 | Khairkhahan et al. |
| 2015/0374976 A1 | 12/2015 | Regnier et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0059002 A1 | 3/2016 | Grubac et al. |
| 2016/0121127 A1 | 5/2016 | Klimovitch et al. |
| 2016/0121128 A1 | 5/2016 | Fishier et al. |
| 2016/0121129 A1 | 5/2016 | Persson et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0317825 A1 | 11/2016 | Jacobson |
| 2016/0367823 A1 | 12/2016 | Cowan et al. |
| 2017/0014629 A1 | 1/2017 | Ghosh et al. |
| 2017/0035315 A1 | 2/2017 | Jackson |
| 2017/0043173 A1 | 2/2017 | Sharma et al. |
| 2017/0043174 A1 | 2/2017 | Greenhut et al. |
| 2017/0189681 A1 | 7/2017 | Anderson |
| 2017/0281261 A1 | 10/2017 | Shuros et al. |
| 2017/0281952 A1 | 10/2017 | Shuros et al. |
| 2017/0281953 A1 | 10/2017 | Min et al. |
| 2017/0281955 A1 | 10/2017 | Maile et al. |
| 2017/0312531 A1 | 11/2017 | Sawchuk |
| 2018/0256902 A1 | 9/2018 | Toy et al. |
| 2018/0256909 A1 | 9/2018 | Smith et al. |
| 2018/0264262 A1 | 9/2018 | Haasl et al. |
| 2018/0264270 A1 | 9/2018 | Koop et al. |
| 2018/0264272 A1 | 9/2018 | Haasl et al. |
| 2018/0264273 A1 | 9/2018 | Haasl et al. |
| 2018/0264274 A1 | 9/2018 | Haasl et al. |
| 2018/0339160 A1 | 11/2018 | Carroll |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 1702648 A2 | 9/2006 |
| EP | 1904166 B1 | 6/2011 |
| EP | 2471452 A1 | 7/2012 |
| EP | 2433675 B1 | 1/2013 |
| EP | 2441491 B1 | 1/2013 |
| EP | 2452721 B1 | 11/2013 |
| EP | 2662113 A3 | 11/2013 |
| EP | 1948296 B1 | 1/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9500202 A1 | 1/1995 |

(56) References Cited

FOREIGN PATENT DOCUMENTS

| | | | |
|---|---|---|---|
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 0234330 A2 | 5/2002 |
| WO | 02098282 A2 | 12/2002 |
| WO | 2005000206 A3 | 1/2005 |
| WO | 2005042089 A1 | 5/2005 |
| WO | 2006065394 A1 | 6/2006 |
| WO | 2006086435 A3 | 8/2006 |
| WO | 2006113659 A1 | 10/2006 |
| WO | 2006124833 A3 | 11/2006 |
| WO | 2007073435 A1 | 6/2007 |
| WO | 2007075974 A2 | 7/2007 |
| WO | 2009006531 A1 | 1/2009 |
| WO | 2012051235 A1 | 4/2012 |
| WO | 2012054102 A1 | 4/2012 |
| WO | 2013080038 A2 | 6/2013 |
| WO | 2013098644 A3 | 7/2013 |
| WO | 2013184787 A1 | 12/2013 |
| WO | 2014120769 A1 | 8/2014 |

OTHER PUBLICATIONS

"Instructions for Use System 1, Leadless Cardiac Pacemaker (LCP) and Delivery Catheter," Nanostim Leadless Pacemakers, pp. 1-28, 2013.

Hachisuka et al., "Development and Performance Analysis of an Intra-Body Communication Device," The 12th International Conference on Solid State Sensors, Actuators and Microsystems, vol. 4A1.3, pp. 1722-1725, 2003.

Seyedi et al., "A Survey on Intrabody Communications for Body Area Network Application," IEEE Transactions on Biomedical Engineering, vol. 60(8): 2067-2079, 2013.

Spickler et al., "Totally Self-Contained Intracardiac Pacemaker," Journal of Electrocardiology, vol. 3(3&4): 324-331, 1970.

Wegmüller, "Intra-Body Communication for Biomedical Sensor Networks," Diss. ETH, No. 17323, 1-173, 2007.

Notification of Transmittal of the International Search Report and the Written Opinion of the International Searching Authority, or the Declaration, dated Jun. 18, 2014, 14 pages.

International Search Report and Written Opinion for Application No. PCT/US2018/015557, 15 pages, dated Apr. 17, 2018.

* cited by examiner

LEADLESS IMPLANTABLE DEVICE WITH DETACHABLE FIXATION

CROSS REFERENCE TO RELATED APPLICATIONS

This application claims the benefit of U.S. Provisional Patent Application Ser. No. 62/450,865 filed on Jan. 26, 2017, the disclosure of which is incorporated herein by reference.

TECHNICAL FIELD

The disclosure is directed to implantable devices such as leadless implantable devices and more particularly to leadless implantable devices with detachable fixation.

BACKGROUND

Implantable medical devices are commonly used today to monitor physiological or other parameters of a patient and/or deliver therapy to a patient. For example, to help patients with heart related conditions, various medical devices (e.g., pacemakers, defibrillators, etc.) can be implanted in a patient's body. Such devices may monitor and in some cases provide electrical stimulation (e.g. pacing, defibrillation, etc.) to the heart to help the heart operate in a more normal, efficient and/or safe manner. In another example, neuro stimulators can be used to stimulate tissue of a patient to help alleviate pain and/or other condition. In yet another example, an implantable medical device may simply be an implantable monitor that monitors one or more physiological or other parameters of the patient, and communicates the sensed parameters to another device such as another implanted medical device or an external device. In some cases, there may be a desire to remove or explant an implanted medical device and to install a replacement implanted medical device.

SUMMARY

The disclosure describes implantable medical devices (IMD), such as but not limited to leadless cardiac pacemakers (LCP), neuro-stimulators (NS), and/or implantable monitors (IM), that are configured to be implanted within the body, sometimes in or near the heart. In some cases, there may be a desire to remove or explant a first IMD and to implant a replacement second IMD. This may be desirable for any number of reasons, such as if a power source of the first IMD has reached its end of life. In some cases, the first IMD may include a fixation portion and a device portion. In some cases, the device portion may make up a majority of the first IMD, and may include a power source such as a battery or the like. After an extended period following implantation, the fixation portion of the first IMD may become entangled or otherwise captured by significant tissue overgrowth, which may make it difficult or undesirable to remove the fixation portion of the IMD. When this happens, the device portion of the first IMD may be disconnected from the fixation portion and removed from the body. The fixation portion may be left in place. In some instances, a second IMD may be implanted at a different location near the remaining fixation portion of the first IMD. In other cases, a device portion of the second IMD may be coupled to the previously installed fixation portion of the first IMD.

In one specific example, an implantable medical device (IMD) may include a fixation module, and a device module that is configured to be releasably connected to the fixation module. The device module may have a proximal end and a distal end, and may include a power source and a controller that is operably coupled to the power source. The controller may be configured to sense cardiac electrical activity via two or more electrodes and deliver pacing pulses via two or more electrodes. The device module may include a first part of a releasable connector. The fixation module may include a plurality of fixation elements for anchoring the fixation module to the patient's heart and a second part of the releasable connector, wherein the first part of the releasable connector and the second part of the releasable connector cooperate to releasably connect the device module with the fixation module. In some instances, the device module may have one or more first fluoroscopic markers and the fixation module having one or more second fluoroscopic markers, wherein the one or more first fluoroscopic markers and the one or more second fluoroscopic markers are arranged so that a predefined alignment between one or more of the first fluoroscopic markers and one or more of the second fluoroscopic markers confirms that the releasable connector is in a fully connected state.

Alternatively or additionally, the device module may further include a proximal electrode and a distal electrode each operatively coupled to the controller, wherein the distal electrode is disposed on an elongated post extending distally from the first part of the releasable connector, and wherein the fixation module defines an aperture through which the elongated post extends to support the distal electrode on a distal side of the fixation module when the releasable connector is in the fully connected state.

Alternatively or additionally, the device module may further include a proximal electrode and a distal terminal each operatively coupled to the controller, and wherein the fixation module includes a distal electrode on a distal side of the fixation module, and wherein the distal terminal of the device module is operatively coupled to the distal electrode of the fixation module when the releasable connector is in the fully connected state.

Alternatively or additionally, the releasable connector may include one or more locking tabs and one more locking slots. The one or more locking tabs may be configured to be moved into the one or more locking slots against a bias mechanism, after which the one or more locking tabs are configured to be rotated relative to the one or more locking slots until one or more of the locking tabs are pushed into one or more retaining recesses by the bias mechanism, at which time the releasable connector is in the fully connected state.

Alternatively or additionally, at least one of the locking tabs and a location of at least one of the retaining recesses are marked by a corresponding fluoroscopic marker.

Alternatively or additionally, the bias mechanism may include a silicone spring seal situated between the device module and the fixation module.

Alternatively or additionally, the releasable connector may include one or more receivers and one or more catches that are biased to extend into and catch one or more of the receivers to form an interference connection when the releasable connector is in the fully connected state.

Alternatively or additionally, the first part of a releasable connector may include the one or more receivers and the second part of a releasable connector may include the one or more catches.

Alternatively or additionally, the releasable connector may further include a seal for sealing the one or more receivers and the one or more catches from an external environment when the releasable connector is in the fully connected state.

Alternatively or additionally, the releasable connector may further include one or more electrical contacts for making an electrical connection between the first part of a releasable connector and the second part of a releasable connector.

In another example, an implantable leadless cardiac pacemaker (LCP) that is configured to pace a patient's heart from a position within a cardiac chamber may include a fixation module that is configured for engagement with the cardiac chamber and a device module that is releasably securable to the fixation module for deployment within the cardiac chamber. The fixation module may include a fixation module housing, a plurality of locking slots, one or more retaining recesses and an aperture that is configured to accommodate an electrode carried by the device module. The device module may include a device module housing and a plurality of locking tabs that are configured to cooperate with the locking slots of the fixation module to releasably secure the device module to the fixation module by inserting the plurality of locking tabs into the locking slots against a bias mechanism, and then rotating the device module relative to the fixation module until one or more of the locking tabs are pushed into one or more of the retaining recesses of the fixation module by the bias mechanism. A power source is disposed within the device module housing. A first electrode may be disposed on the device module housing and a second electrode may be disposed on an elongated post extending distally of the plurality of locking tabs, the elongated post configured to extend through the aperture in the fixation module housing to place the second electrode in a position where the second electrode can contact cardiac tissue when the device module is engaged with the fixation module and the LCP is implanted. A controller may be disposed within the device module housing and may be operably coupled to the power source, the controller configured to sense cardiac electrical activity and to deliver pacing pulses via one or more of the first electrode and the second electrode.

Alternatively or additionally, the fixation module may further include a plurality of fixation tines that are configured to extend distally into the patient's cardiac tissue and then back proximally to hook the patient's cardiac tissue to thereby anchor the fixation module to the patient's heart.

Alternatively or additionally, the bias mechanism may be a resilient seal that is configured to engage corresponding mating surface on the fixation module housing and the device module housing.

Alternatively or additionally, one or more of the locking tabs of the device module may include a fluoroscopic marker, and the fixation module may include one or more fluoroscopic markers secured relative to the fixation module housing, the one or more fluoroscopic markers of the fixation module may be configured to indicate an orientation of the fixation module relative to the locking tabs of the device module under fluoroscopy.

In another example, an implantable leadless cardiac pacemaker (LCP) that is configured to pace a patient's heart from a position within a cardiac chamber includes a fixation module that is configured for engagement with the cardiac chamber and a device module that is releasably securable to the fixation module for deployment within the cardiac chamber. The device module includes a device module housing and an elongated post that extends distally from the device module housing and that includes one or more receivers and one or more electrical contacts. The fixation module includes a fixation module housing and one or more electrodes on a distal side of the fixation module housing. The fixation module includes a post receiving aperture for receiving the elongated post of the device module as well as one or more catches that are biased to extend into and catch one or more of the receivers of the elongated post when the elongated post is received by the post receiving aperture. The fixation module includes one or more electrical contacts for making an electrical connection with one or more of the electrical contacts of the elongated post when the elongated post is received by the post receiving aperture, wherein one or more of the electrical contacts of the fixation module are operatively coupled to one or more of the electrodes on the distal side of the fixation module housing.

Alternatively or additionally, the LCP may further include a seal for providing a seal between the elongated post of the device module and the fixation module for sealing the one or more electrical contacts of the fixation module from an external environment when the elongated post is received by the post receiving aperture.

Alternatively or additionally, the one or more receivers may include one or more grooves formed in an outer surface of the elongated post.

Alternatively or additionally, the one or more catches may include a coil spring that is biased to extend into and catch one or more of the grooves of the elongated post.

Alternatively or additionally, the one or more catches may include a leaf spring that is biased to extend into and catch one or more of the grooves of the elongated post.

Alternatively or additionally, the LCP may further include one or more fluoroscopic markers for indicating if the elongated post is sufficiently received by the post receiving aperture to be in a fully connected state.

The above summary of some embodiments is not intended to describe each disclosed embodiment or every implementation of the present disclosure. The Figures and Detailed Description, which follow, more particularly exemplify these embodiments.

BRIEF DESCRIPTION OF THE FIGURES

The disclosure may be more completely understood in consideration of the following description of in connection with the accompanying drawings, in which.

Figure 1:
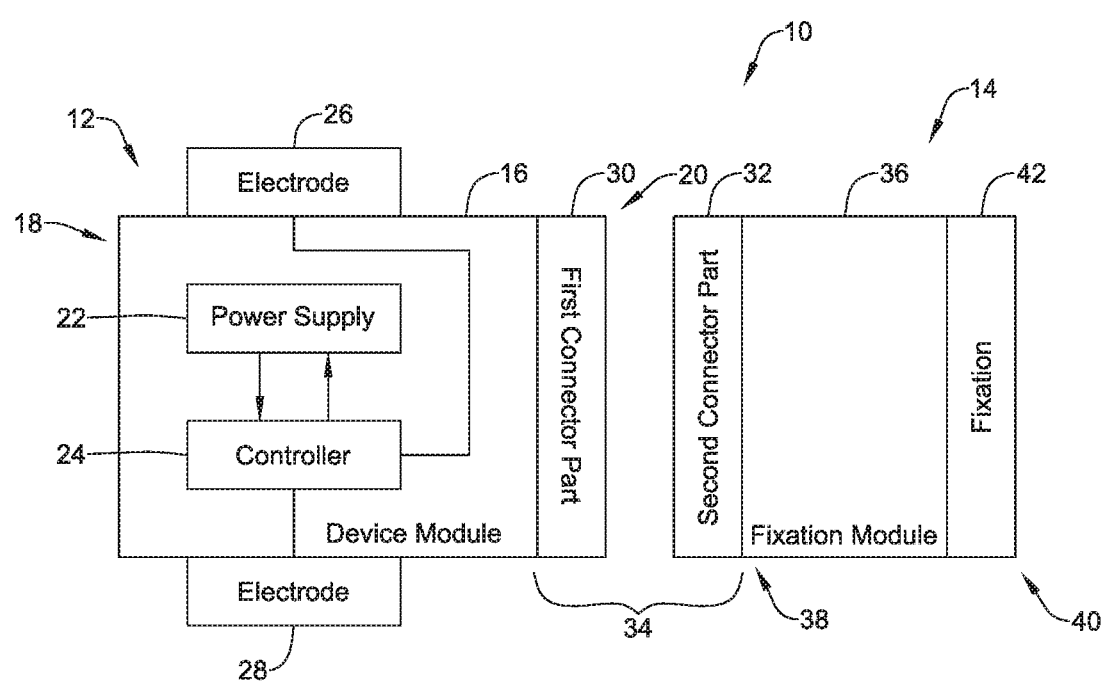
FIG. 1 is a schematic block diagram of an illustrative implantable medical device (IMD) in accordance with the disclosure.
Figure 2:
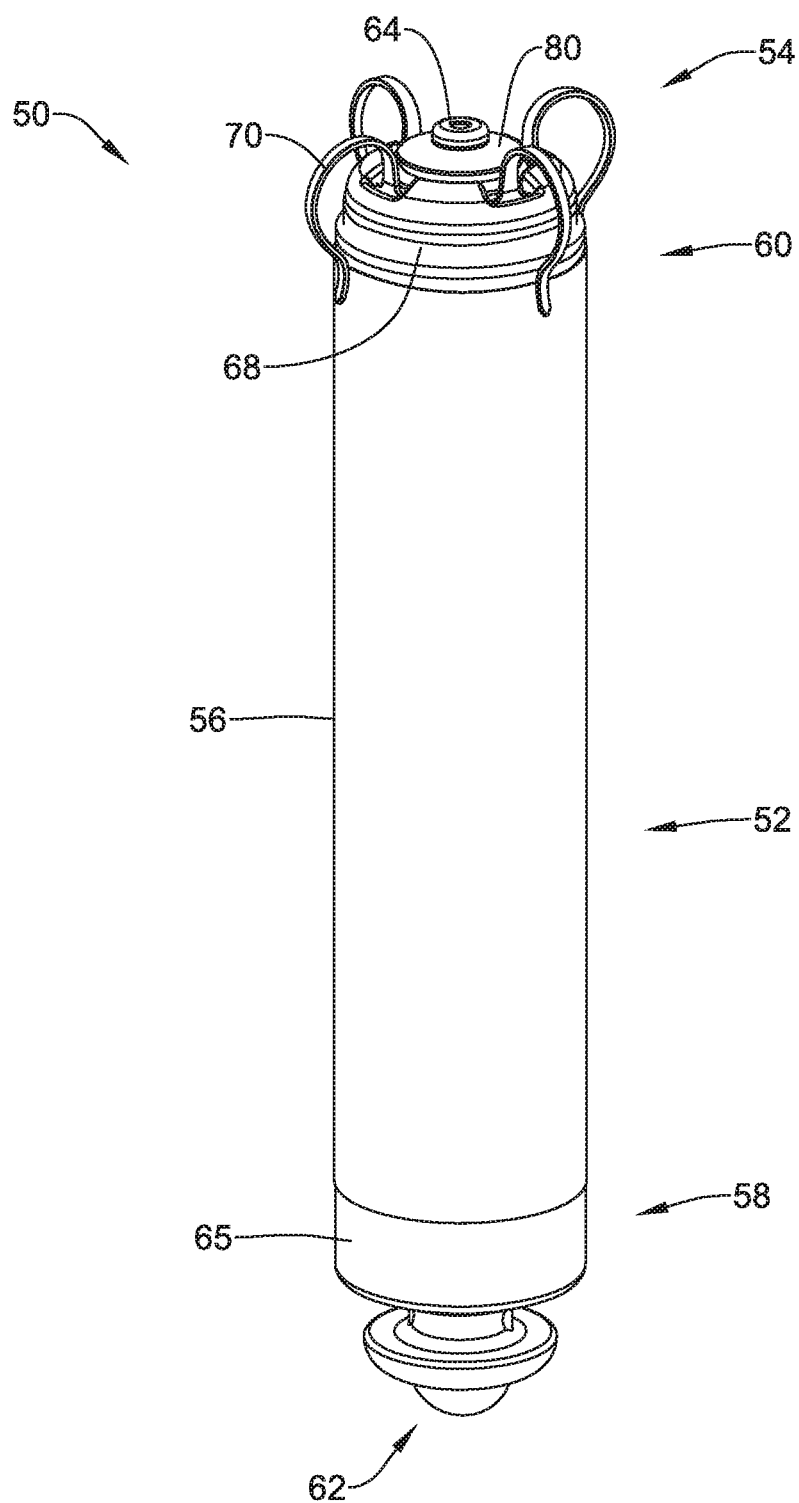
FIG. 2 is a side view of an implantable leadless cardiac pacemaker (LCP) as an example of the IMD of FIG. 1.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

The disclosure is directed to implantable medical devices (IMD) that may include a device module and a fixation module. In some cases, the IMD may be implanted with the device module secured to the fixation module and thus may be provided as a single structure and may be implanted using any desired implantation technique and/or delivery device. In some cases, after the IMD has been implanted, there may be a desire to remove the IMD and/or to replace the IMD. For example, an IMD may be removed and replaced when the power source (e.g. battery) in the implanted IMD has reached the end of its expected life. In some cases, the fixation portion of an IMD may be located at a good site for pacing and/or sensing, and there may be interest in being able to place the replacement IMD at the same location. In some instances, due to tissue ingrowth and the like, the fixation portion of the IMD may be difficult to remove. Accordingly, in some cases, the device module may be removed from the fixation module and removed from the patient. In some instances, a new device module may be delivered and secured to the previously implanted fixation module. In some cases, the previously implanted fixation module may simply be left in place, and a new IMD having a new device module and a new fixation module may be delivered and implanted at a new implantation site. These are just examples.

Turning to FIG. 1, an implantable medical device (IMD) 10 is shown. The illustrative IMD 10 includes a device module 12 and a fixation module 14. It will be appreciated that FIG. 1 is highly schematic. The device module 12 has a device housing 16 that extends from a proximal end 18 to a distal end 20. The illustrative device module 12 includes a power supply 22 and a controller 24 that is operably coupled to the power supply 22. In some cases, the controller 24 may be configured to sense cardiac electrical activity via two or more electrodes and to deliver pacing pulses via two or more electrodes that may be the same as those used to sense cardiac electrical activity or that may be different than those used to sense cardiac electrical activity. The device module 12 is illustrated as having a first electrode 26 and a second electrode 28. It will be appreciated that the first electrode 26 and the second electrode 28 may be disposed at any desired location or position relative to the device housing 16, and in some cases, may be located on the proximal end 18 and/or distal end 20. In some cases, there may be additional electrodes as well.

In some instances, as will be discussed with respect to subsequent Figures, at least one of the first electrode 26 and the second electrode 28 may be disposed at or even extend distally beyond the distal end 20 of the device housing 16. In some cases, at least one of the first electrode 26 and the second electrode 28 may extend distally from the device module 12 a distance sufficient to permit the electrode to extend through the fixation module 14 and contact tissue. In some instances, at least one of the first electrode 26 and the second electrode 28 may actually be secured to the fixation module 14. FIGS. 2 through 7 provide examples of an IMD in which an electrode extends distally from the device module 12 and through the fixation module 14 to contact tissue. FIGS. 8 through 15 provide examples of an IMD in which an electrode is secured to the fixation module 14, and the fixation module 14 operatively connects the distal electrode of the device module to an electrode of the fixation module 14.

In FIG. 1, the device module 12 also includes a first connector part 30 and the fixation module 14 includes a second connector part 32. In some cases, the first connector part 30 and the second connector part 32 may, in combination, be considered as forming a releasable connector 34. In some cases, the first connector part 30 and the second connector part 32 cooperate to releasably connect the device module 12 with the fixation module 14. The fixation module 14 may be considered as having a fixation housing 36 extending from a proximal end 38 to a distal end 40. The second connector part 32 may be secured to the proximal end 38 of the fixation housing 36. A fixation structure 42 may be secured to the distal end 40 of the fixation housing 36. In some cases, the fixation structure 42 may schematically represent an active fixation structure such as a fixation helix. In some instances, the fixation structure 42 may schematically represent a passive fixation structure such as fixation tines. Subsequent Figures will provide examples of fixation tines.

In some cases, as will be shown in subsequent Figures, the device module 12 may include one or more first fluoroscopic markers and the fixation module 14 may include one or more second fluoroscopic markers. The one or more first fluoroscopic markers and the one or more second fluoroscopic markers may be arranged so that a predefined alignment between one or more of the first fluoroscopic markers and one or more of the second fluoroscopic markers confirms that the releasable connector 34 is in a fully connected state and/or a fully disconnected state.

Figure 3:
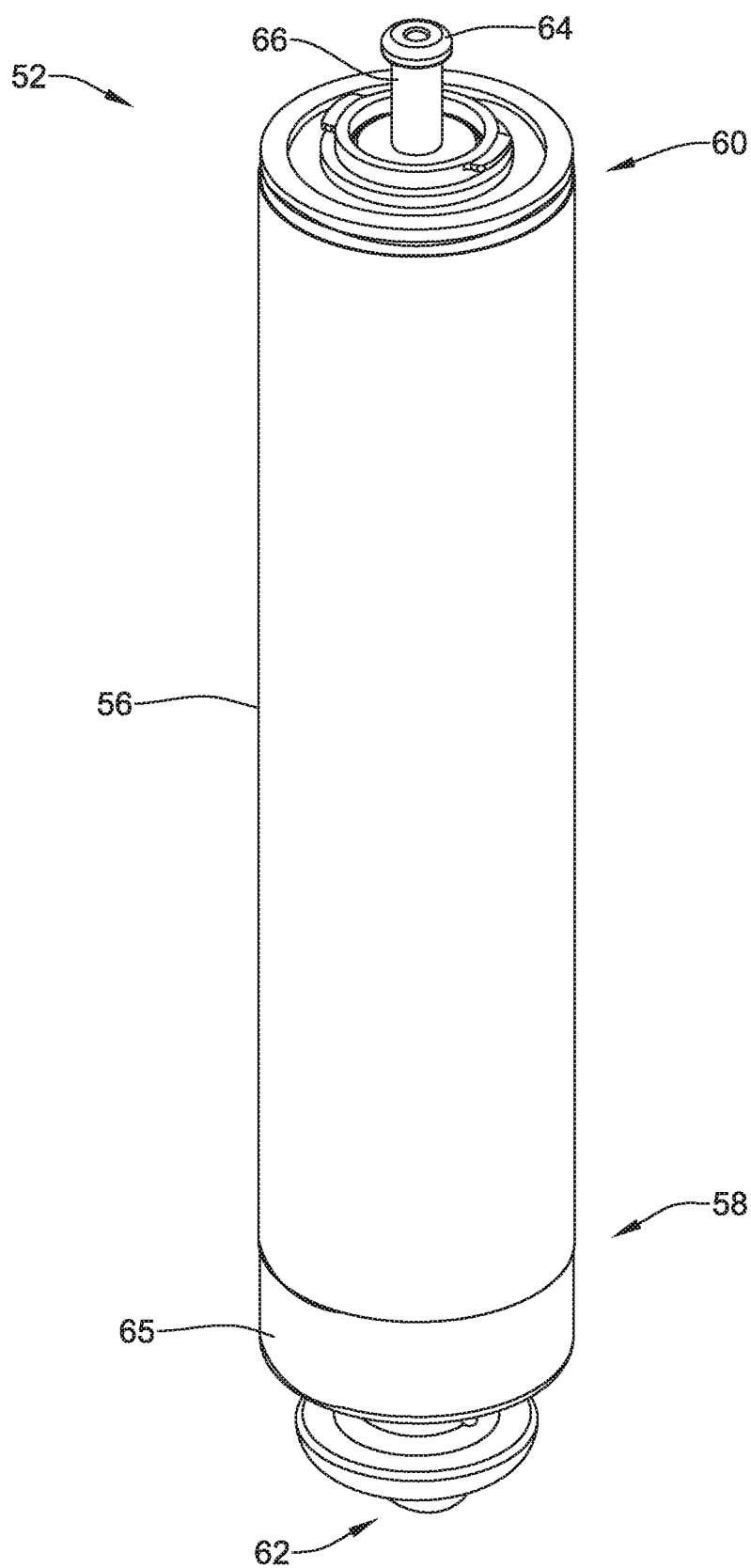
FIG. 3 is a side view of a device module forming a portion of the LCP of FIG. 2.
Figure 4:
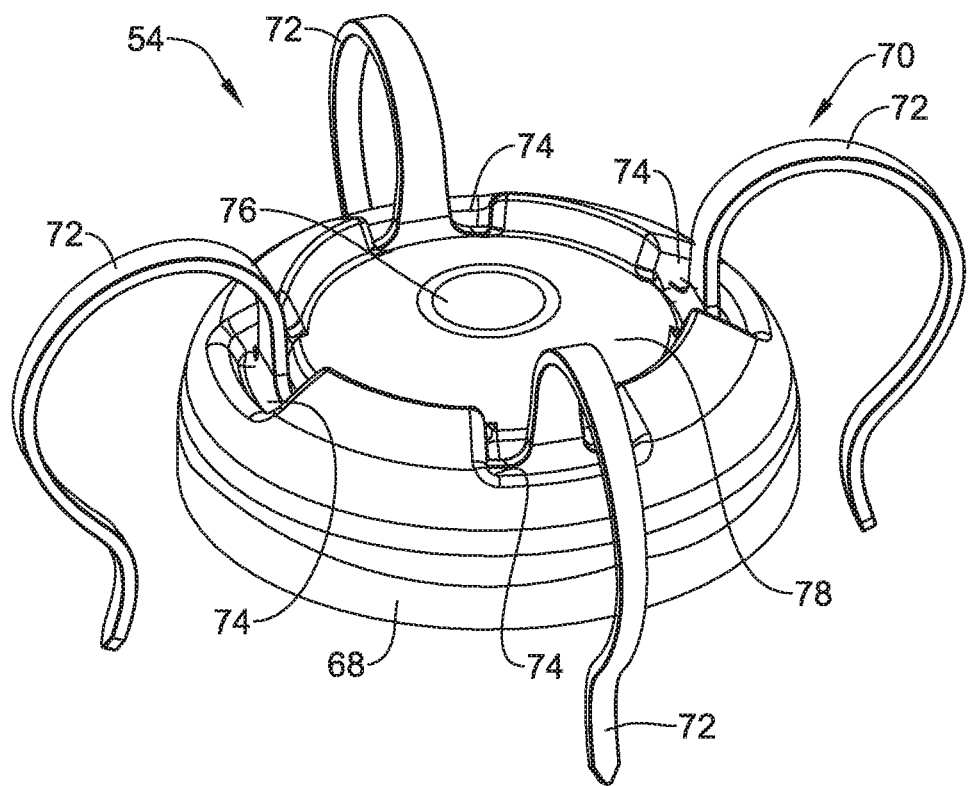
FIG. 4 is a perspective view of a fixation module forming a portion of the LCP of FIG. 2.

FIGS. 2 through 7 illustrate an IMD 50 that may be considered as being a leadless cardiac pacemaker (LCP). The illustrative IMD 50 includes a device module 52, shown separately in FIG. 3, and a fixation module 54, shown separately in FIG. 4. The device module 52 includes a device housing 56 extending from a proximal end 58 to a distal end 60. The illustrative device module 52 includes a retrieval feature 62 secured relative to the proximal end 58. At the distal end 60, the device module 52 is coupled to the fixation module 54. In some cases, as best seen in FIG. 3, the device module 52 may include a distal electrode 64 extending distally on a distal post 66. The distal electrode 64 may be operably coupled to the controller 24 (FIG. 1). The device module 52 may also include a proximal electrode 65 that is operably coupled to the controller 24 (FIG. 1). As shown, the proximal electrode 65 may be a ring electrode, but this is not required in all cases. The distal post 66 provides a mechanical and electrical connection between the distal electrode 64 and the controller 24, and the distal post 66 is dimensioned to allow the distal electrode 64 to extend distally from the fixation module 54 when the fixation module is releasably connected to the device module 52.

As illustrated, the fixation module 54 includes a fixation housing 68 and a fixation tines assembly 70. In some cases, the fixation tines assembly 70 may include one or more passive fixation tines 72 (four are shown) that extend through corresponding apertures 74 formed within the fixation housing 68. In some cases the passive fixation tines 72 are coupled to or integrally formed with a ring 73 (FIG. 6) that joins the passive fixation tines 72 together underneath the fixation housing 68 and helps secure the passive fixation tines 72 to each other and in place relative to the fixation housing 68. As seen for example in FIG. 4, the fixation housing 68 may include a central aperture 76 that is sized to accommodate the distal electrode 64, and may in some cases include a recessed portion 78 that may be dimensioned to accommodate a drug collar 80 (shown in FIG. 2).

Figure 5:
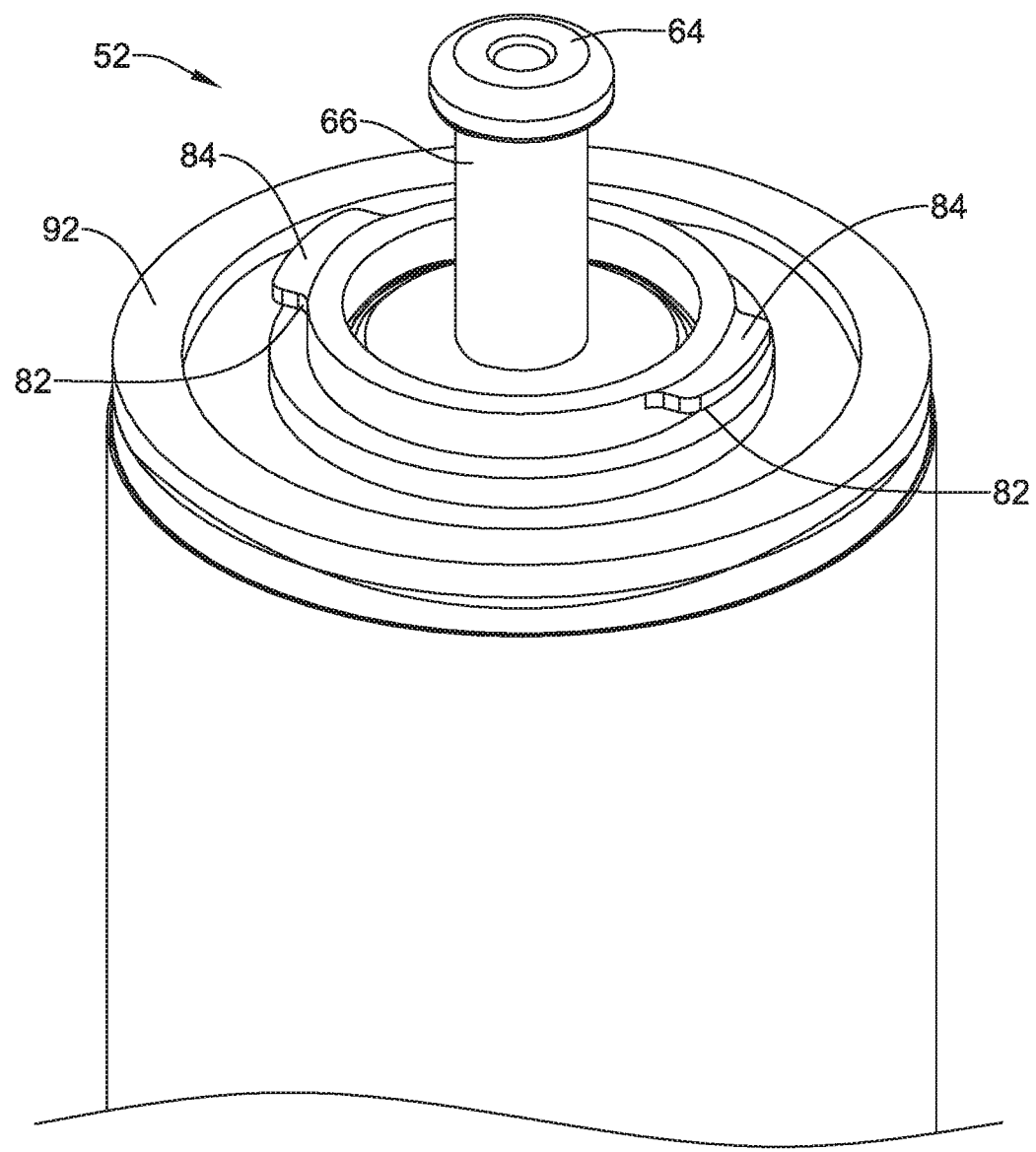
FIG. 5 is a perspective end view of the device module of FIG. 3.
Figure 6:
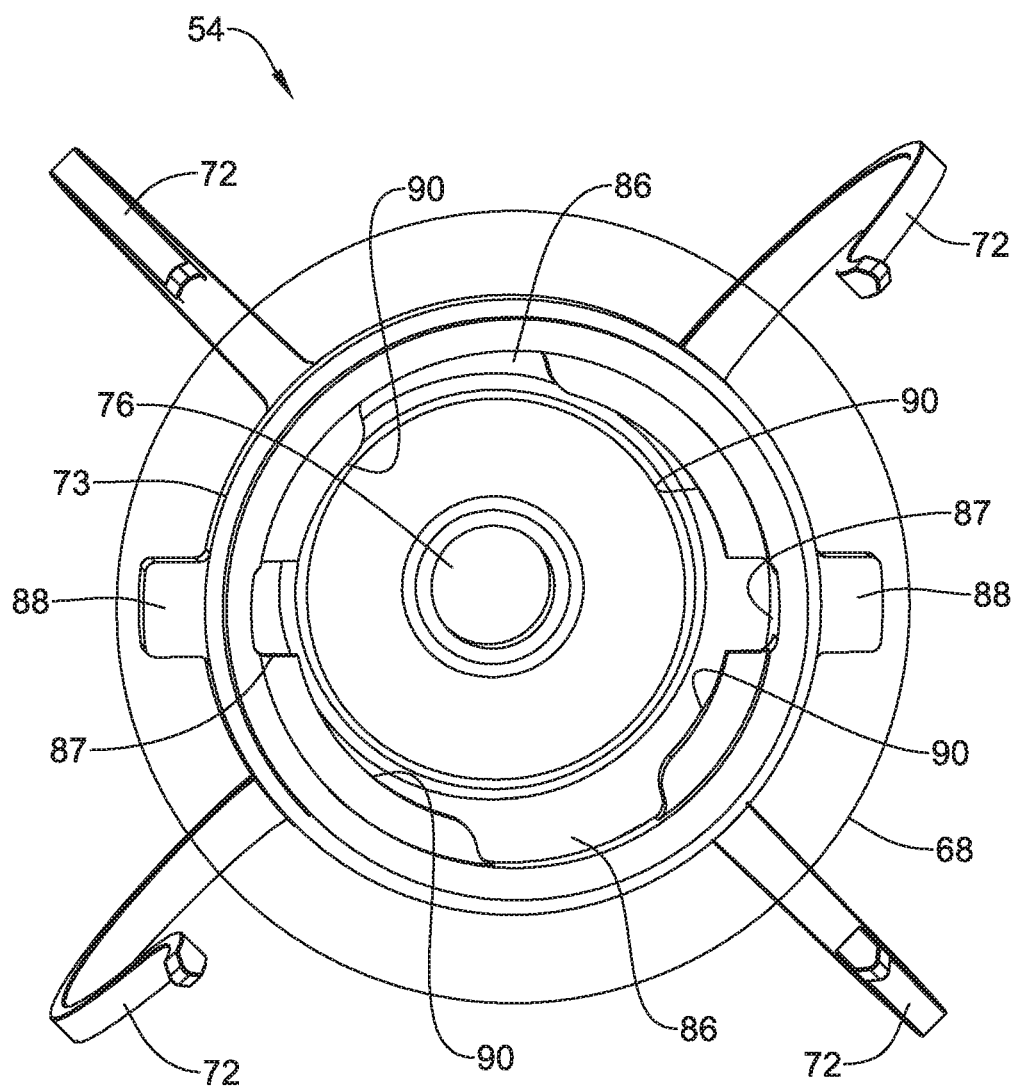
FIG. 6 is a bottom perspective view of the fixation module of FIG. 4.
Figure 7:
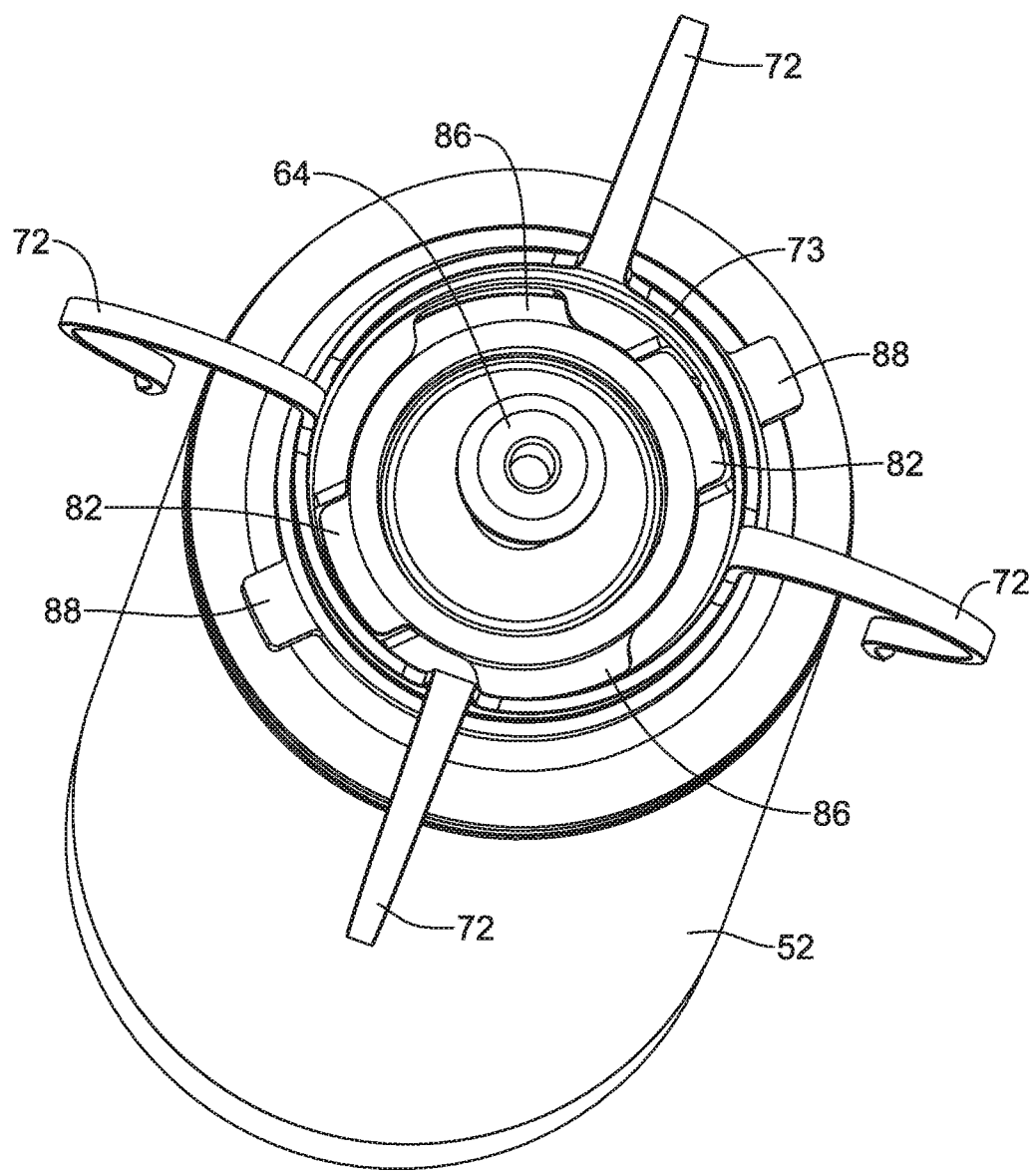
FIG. 7 is an end view of the LCP of FIG. 2, with portions shown as transparent to reveal internal details.

FIGS. 5 through 7 provide additional details regarding how the device module 52 may be releasably coupled to the fixation module 54. In some cases, the device module 52 includes one or more locking tabs 82. While a pair of locking tabs 82 are illustrated, in some cases there may be three or more locking tabs 82. In some cases, each of the one or more locking tabs 82 may include a fluoroscopic marker 84. As can be seen in FIG. 6, the fixation module 54 may include one or more corresponding locking slots 86. While a pair of locking slots 86 are shown, in some cases there may be three or more locking slots 86 in order to accommodate however many locking tabs 82 are present on the device module 52. In some instances, a fluoroscopic marker 88 may be disposed radially outwardly from each of the one or more locking slots 86 in order to help visualize the location of the one or more locking slots 86 under fluoroscopy.

In the example shown, the one or more locking slots 86 are separated by retention structures 90. In some cases, the device module 52 may be secured to the fixation module 54 by aligning the one or more locking tabs 82 with the corresponding one or more locking slots 86. As will be appreciated, this may be done by visually aligning (under fluoroscopy) the fluoroscopic markers 84 (on the one or more locking tabs 82) with the fluoroscopic markers 88 (adjacent to the one or more locking slots 86). Once the one or more locking tabs 82 are aligned with the corresponding one or more locking slots 86, the device module 52 may be secured in place by moving the device module 52 distally relative to the fixation module 54 such that the one or more locking tabs 82 penetrate into the one or more locking slots 86. The device module 52 may then be rotated relative to the fixation module 54 to move the one or more locking tabs 82 into position beneath the retention structures 90. In some cases, the device module 52 may be rotated 90 degrees. In some cases, the one or more locking tabs 82 are held in position at one or more corresponding retention recesses 87.

In some cases, pushing the device module 52 distally relative to the fixation module 54 involves pushing against a bias mechanism that will, as can be appreciated, help to hold the one or more locking tabs 82 in position against the retention structures 90, and thus help to prevent accidental separation of the device module 52 from the fixation module 54, particularly after implantation. In some cases, the bias mechanism may be a silicone spring seal 92 that is secured to the device module 52. In some cases, the retention structures 90 may themselves include retaining recesses that the one or more locking tabs 82 may fit into and be held in place by the bias mechanism.

In some cases, each of the one or more locking tabs 82 may be considered as being catches, and a back side of the retention structures 90 may include one or more receivers, where each of the catches are biased to extend into the receivers to form an interference connection when the device module 52 is fully connected to the fixation module 54. FIG. 7 shows the completed assembly, with the fixation housing 68 shown as being transparent so that the relative arrangement of the one or more locking tabs 82 and the corresponding one or more locking slots 86 may be seen.

FIGS. 8 through 15 illustrate an IMD 100 that may be considered as being a leadless cardiac pacemaker (LCP). The illustrative IMD 100 includes a device module 102, shown separately in FIG. 9, and a fixation module 104, shown separately in FIG. 10. The device module 102 includes a device housing 106 extending from a proximal end 108 to a distal end 110. The illustrative device module 102 includes a retrieval feature 112 secured relative to the proximal end 108. At the distal end 110, the device module 102 is coupled to the fixation module 104. In some cases, as shown, the device module 102 includes a proximal electrode 115 that is operably coupled to the controller 24 (FIG. 1). As shown, the proximal electrode 115 is a ring electrode, but this is not required in all cases. In some cases, the fixation module 104 includes a distal electrode 114 that is operably coupled to the controller 24.

As illustrated, the fixation module 104 includes a fixation housing 118 and a fixation tines assembly 70. In some cases, the fixation tines assembly 70 may include one or more passive fixation tines 72 (four are shown) that extend through corresponding apertures 74 formed within the fixation housing 118. In some cases, although not expressly shown here, the passive fixation tines 72 are coupled to or integrally formed with a ring that joins the passive fixation tines 72 together underneath the fixation housing 118 and that helps to secure the passive fixation tines 72 to each other and in place relative to the fixation housing 118. See, for example, the ring 73 referenced previously with respect to FIG. 6. In some cases, a drug collar 130 (see FIG. 8) may be disposed relative to the fixation housing 118.

Because the distal electrode 114 is secured relative to the fixation module 104, rather than directly to the device module 102, there is a need to provide an electrical connection between the controller 24 (FIG. 1), in the device module 102, and the distal electrode 114. As can be seen for example in FIGS. 9 and 12, the illustrative device module 102 includes a distal terminal 140 that is operably coupled to the controller 24 and extends distally from the distal end 110 of the device housing 106. In some cases, as shown, the distal terminal 140 may have a tapered distal end 142 to facilitate insertion into the fixation module 104. A detent 144 may be used, as will be discussed, to also provide a releasable mechanical connection between the device module 102 and the fixation module 104. In some cases, the distal terminal 140 may include one or more seals 146 in order to help prevent fluids from bridging conductors and/or causing a short to body fluids (e.g. blood). At least the distal end 142 may be considered as being electrically active. In some cases, if desired, a secondary seal 148 may be located at or near the distal end 110.

Figure 11:
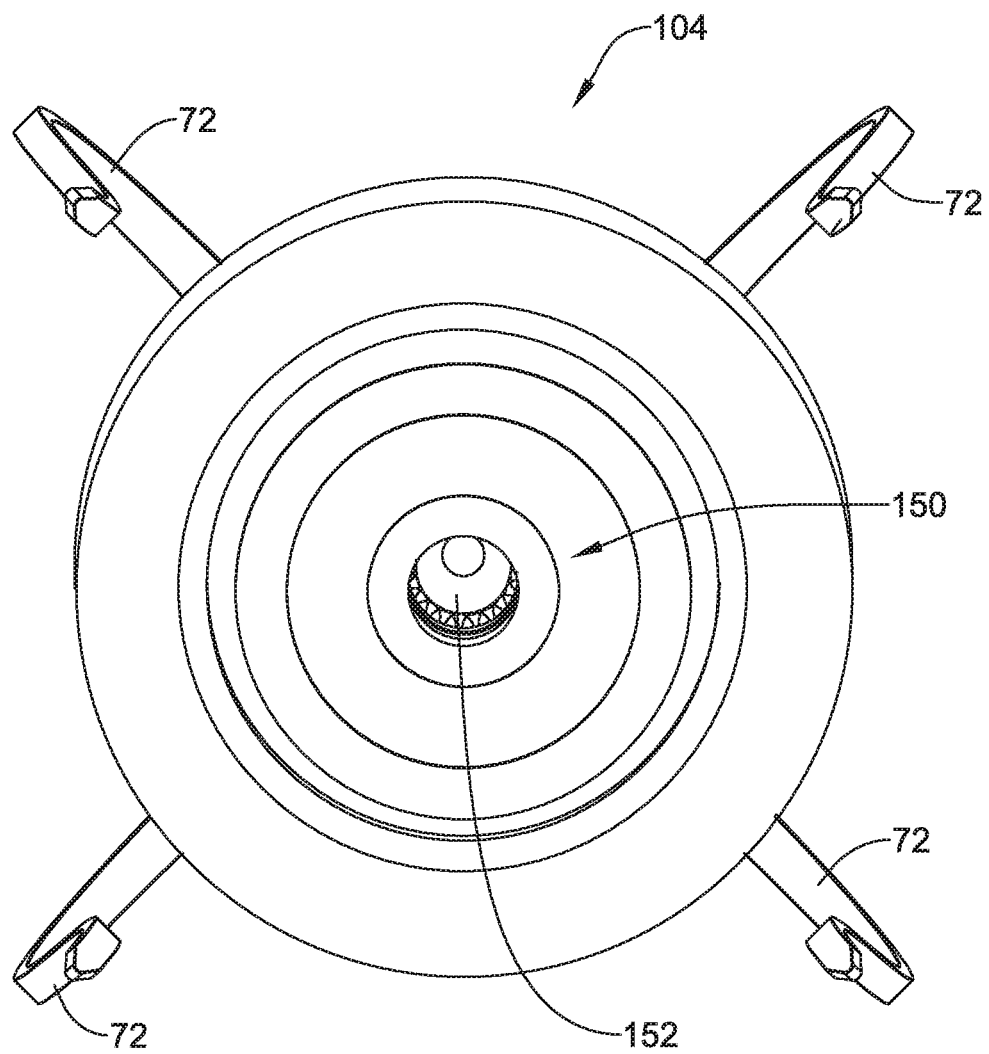
FIG. 11 is a bottom perspective view of the fixation module of FIG. 10.
Figure 12:
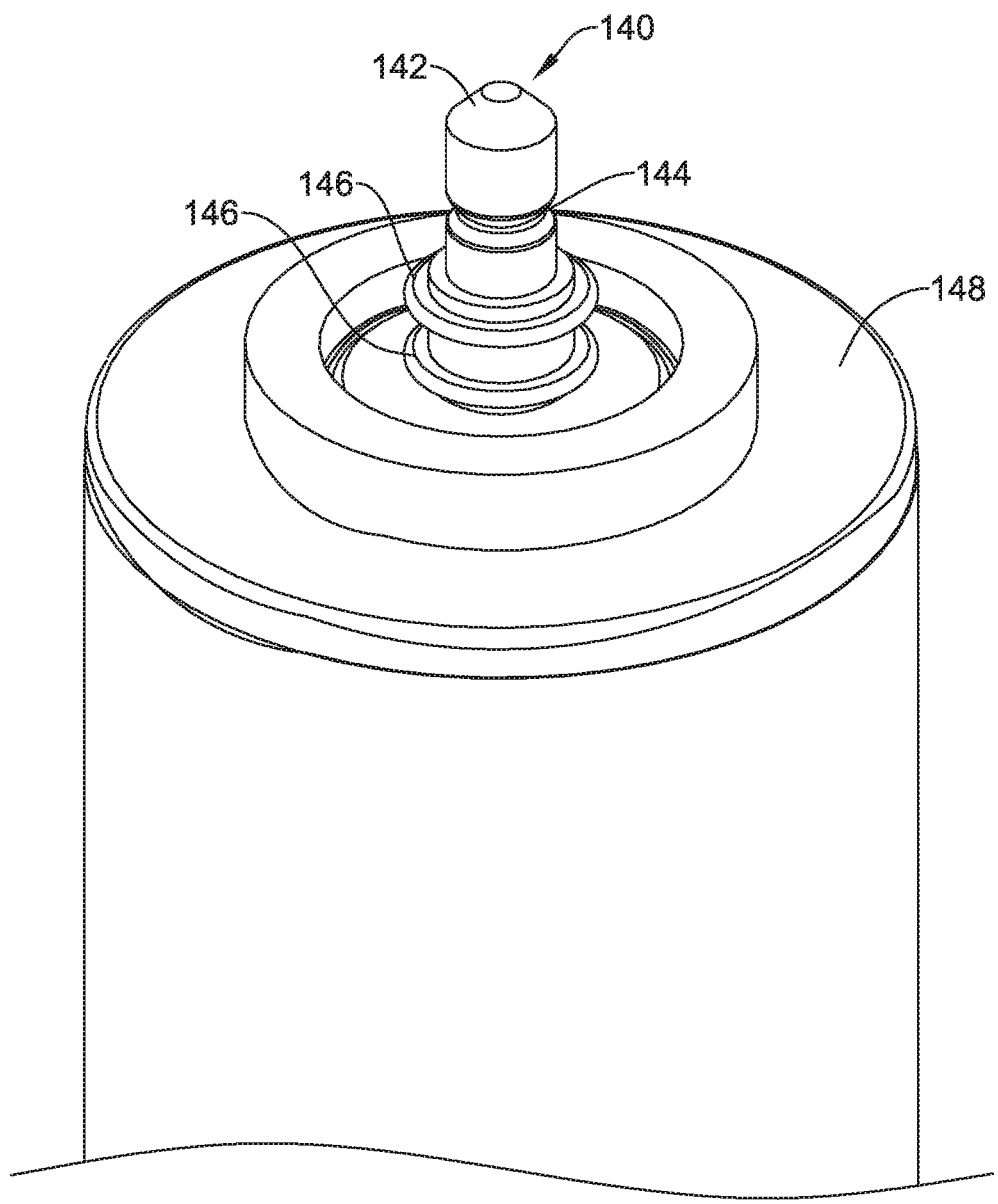
FIG. 12 is a perspective end view of the device module of FIG. 9.
Figure 13:
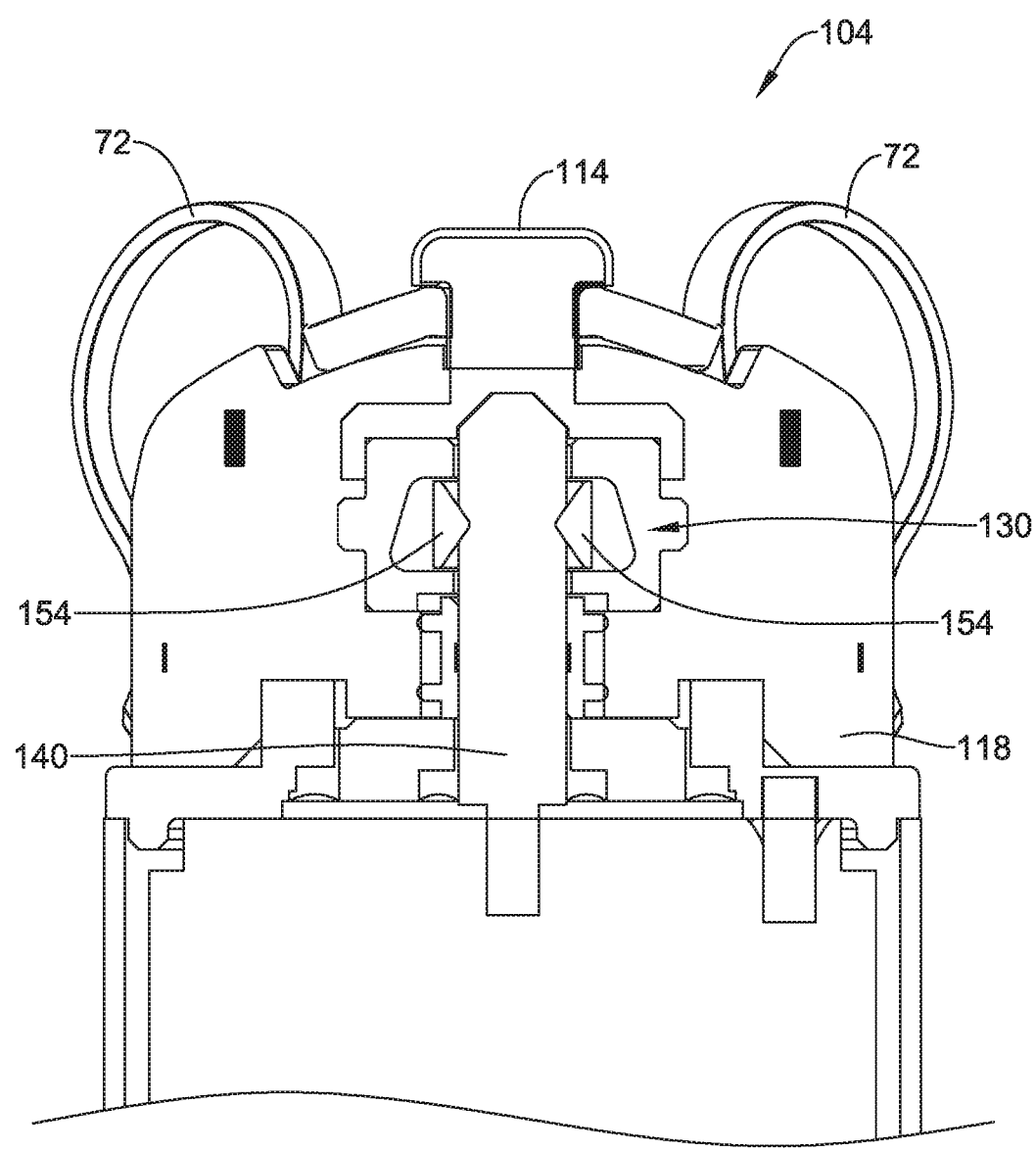
FIG. 13 is an example schematic cross-sectional view taken through the distal end of the LCP of FIG. 8.
Figure 14:
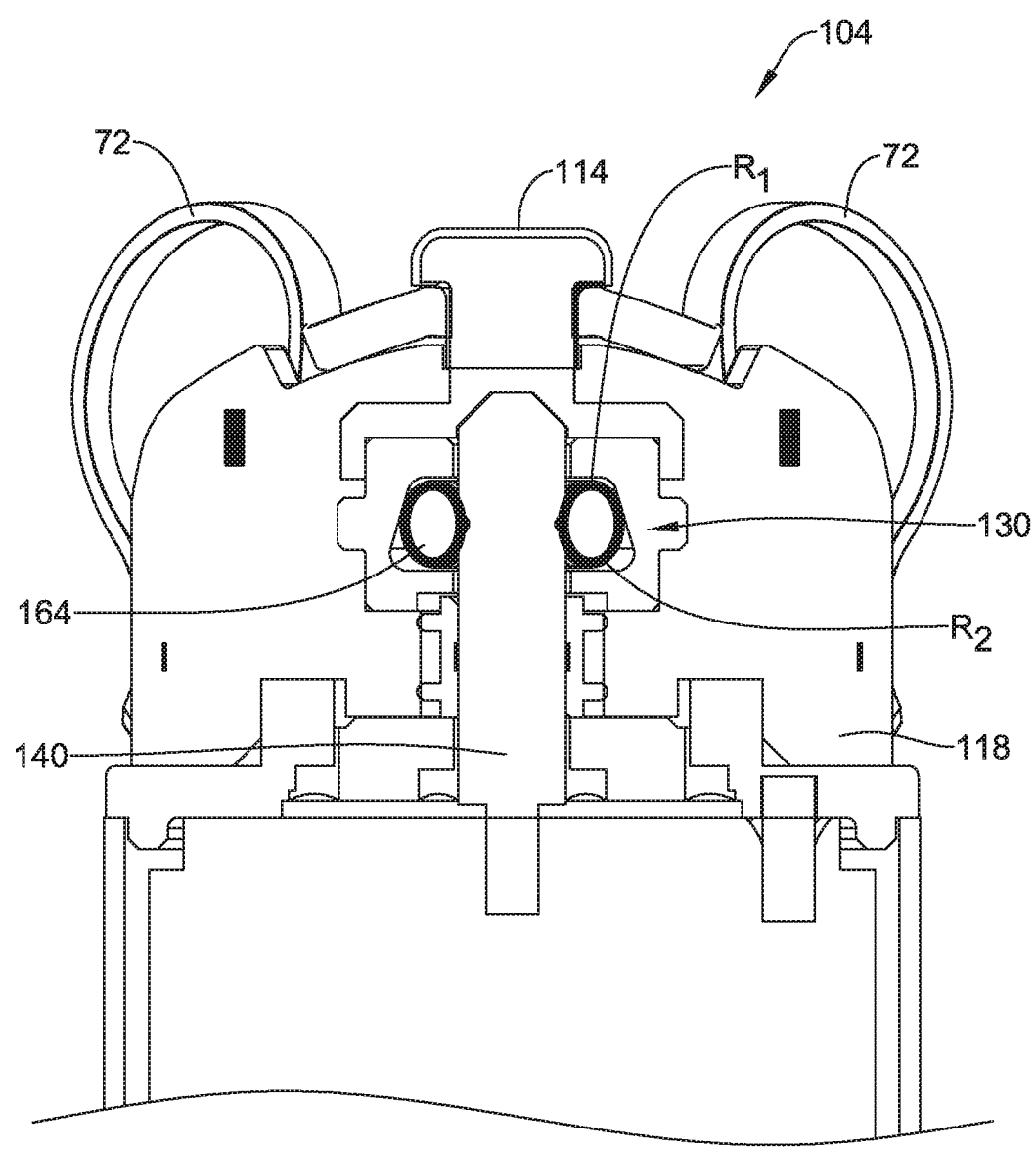
FIG. 14 is another example schematic cross-sectional view taken through the distal end of the LCP of FIG. 8.

As can be seen for example in FIGS. 11, 13 and 14, the fixation module 104 may include a connection assembly 150. In some cases, for example, the distal terminal 140 (part of the device module 102) may be considered as a first connector part and the connection assembly 150 (part of the fixation module 104) may be considered as a second connector part. The first connector part and the second connector part may, for example, be considered as forming a releasable connector that provides an electrical connection between the controller 24 (FIG. 1) and the distal electrode 114 as well as providing a mechanical connection between the device module 102 and the fixation module 104.

The illustrative connection assembly 150 includes an aperture 152 (best seen in FIG. 11) that is configured to accommodate the distal terminal 140. As shown in FIG. 13, in some cases the connection assembly 150 includes leaf spring contacts 154 that help to provide an electrical connection between the distal terminal 140 and the distal electrode 114. The leaf spring contacts 154 may be positioned such that they extend into the detent 144. The leaf spring contacts 154 may be configured to flex as the distal terminal 140 is inserted through the aperture 152 and into the connection assembly 150 and then may snap into the detent 144. The leaf spring contacts 154, once snapped into the detent 144, may be considered as a suitable releasable mechanical connection between the device module 102 and the fixation module 104 that secures the device module 102 to the fixation module 104 against accidental separation but permits separation when desired.

FIG. 14 shows an example in which the connection assembly 150 includes a toroidal coil spring contact 164. The coil spring contact 164 may be configured to flex as the distal terminal 140 is inserted through the aperture 152 and into the connection assembly 150 and may snap into the detent 144. It will be appreciated that this may provide a mechanical connection between the device module 102 and the fixation module 104. The coil spring contact 164, once snapped into the detent 144, may be considered as a suitable releasable mechanical connection between the device module 102 and the fixation module 104 that secures the device module 102 to the fixation module 104 against accidental separation but permits separation when desired. In some cases, the coil spring contacts 164 may be configured to have a relatively lower insertion force and a relatively higher withdrawal force in order to facilitate assembly but discourage accidental disassembly. This may be accomplished by having a toroidal coil spring that is formed by a wound wire, wherein the wound wire is bent to have a smaller radius $R_1$ along the top of the donut shaped coil spring than the radius $R_2$ along the bottom of the donut shaped coil spring. This is just one example.

Figure 15:
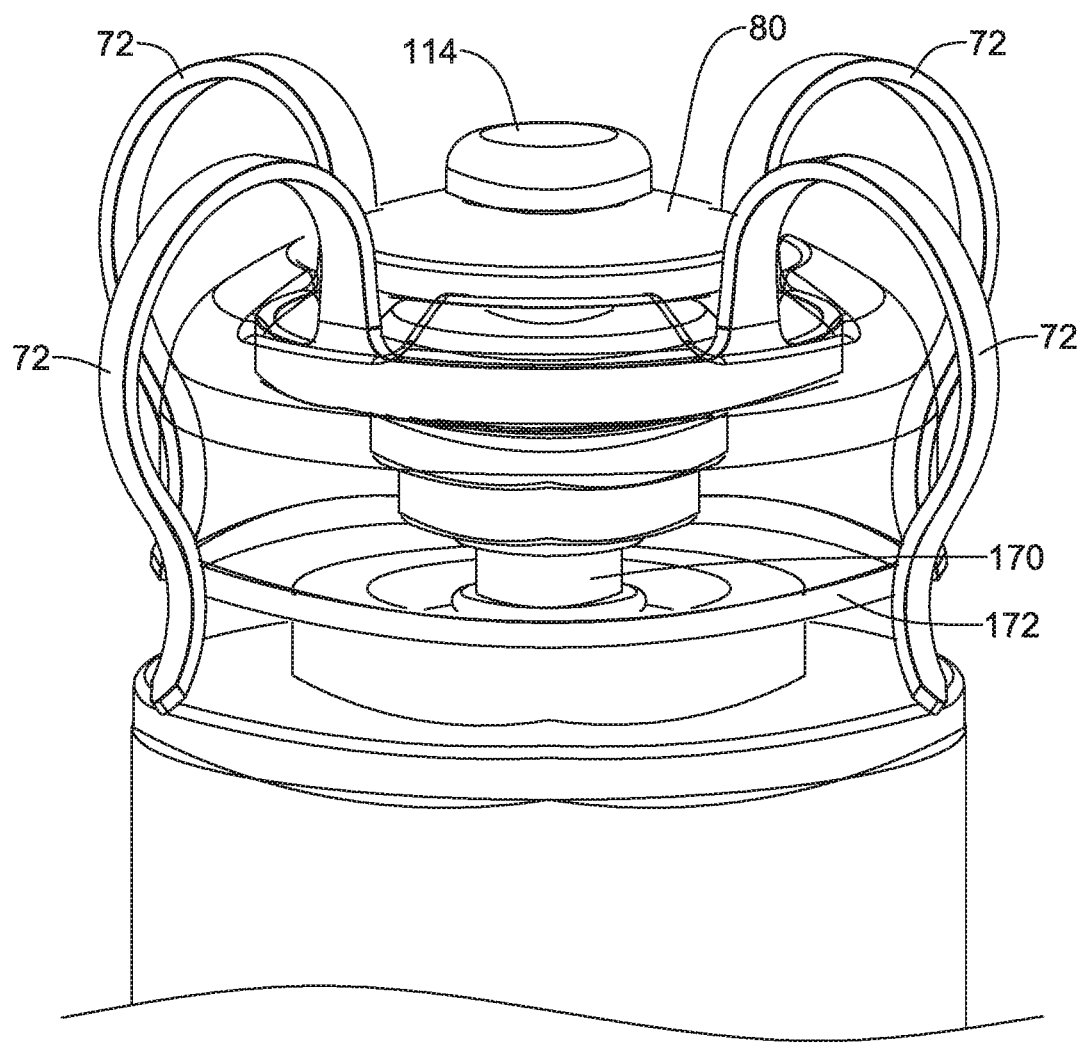
FIG. 15 is an end view of the LCP of FIG. 8, with portions shown as transparent to reveal internal details.

FIG. 15 is a perspective view of a portion of the IMD 100, with the fixation housing 118 shown as being transparent in order to see internal details. In particular, there may be a first fluoroscopic ring 170 secured to the distal terminal 140 and a second fluoroscopic ring 172 secured to the fixation housing 118. As the device module 102 is being inserted into the fixation module 104, the first fluoroscopic ring 170 will be mis-aligned with the second fluoroscopic ring 172, but will become closer to the second fluoroscopic ring 172 as the device module 102 is inserted toward the fully connected state (e.g. the leaf spring contacts 154 snap into the detent 144 or the coil spring contact 164 snaps into the detent 144). When the first fluoroscopic ring 170 is axially aligned with the second fluoroscopic ring 172, this is an indication that the device module 102 is fully inserted into the fixation module 104. In some cases, depending on the relative angle at which this is being viewed, the first fluoroscopic ring 170 and the second fluoroscopic ring 172 may appear either brighter or darker, depending on whether a positive image or a negative image was being displayed by the fluoroscope.

Figure 8:
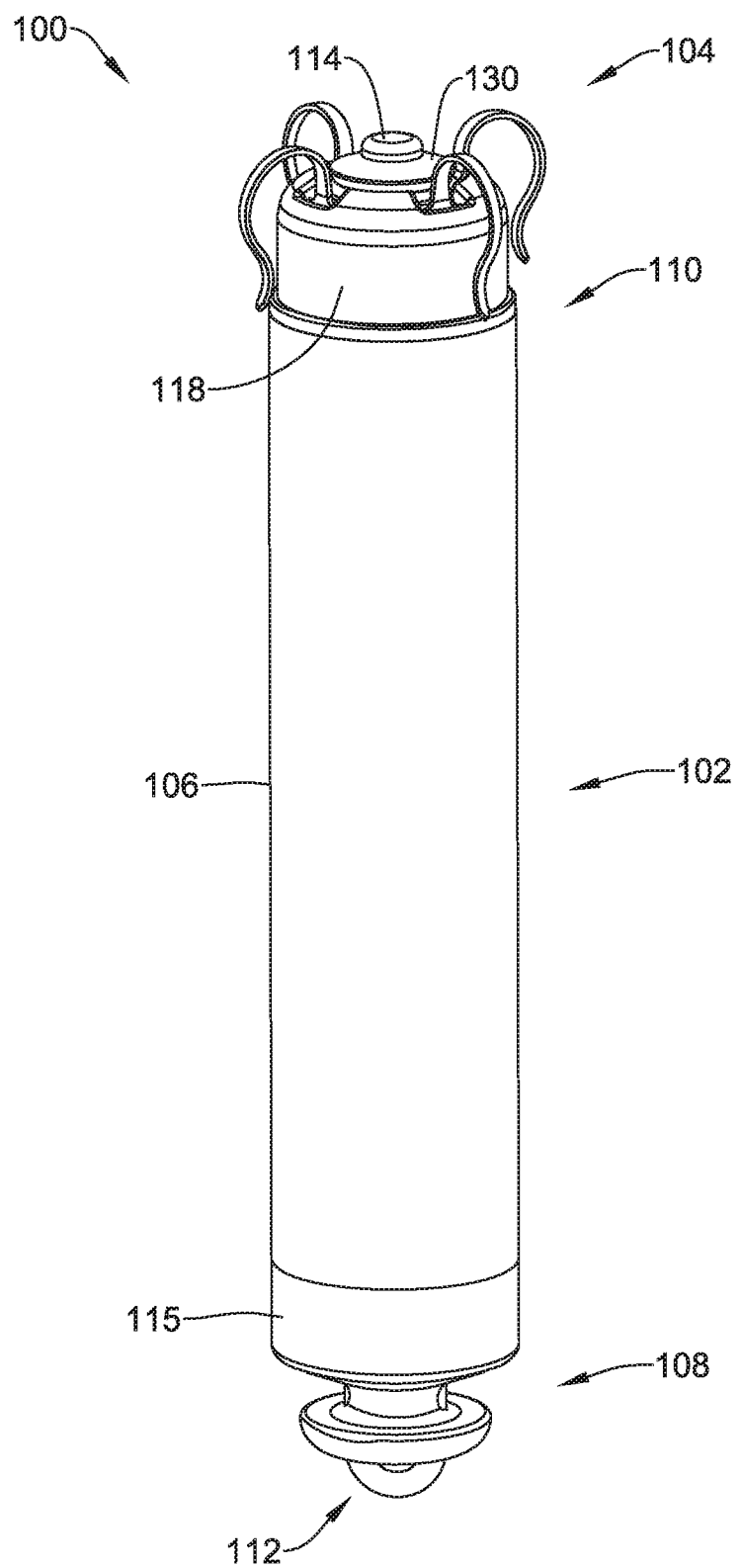
FIG. 8 is a side view of an LCP as another example of the IMD of FIG. 1.
Figure 9:
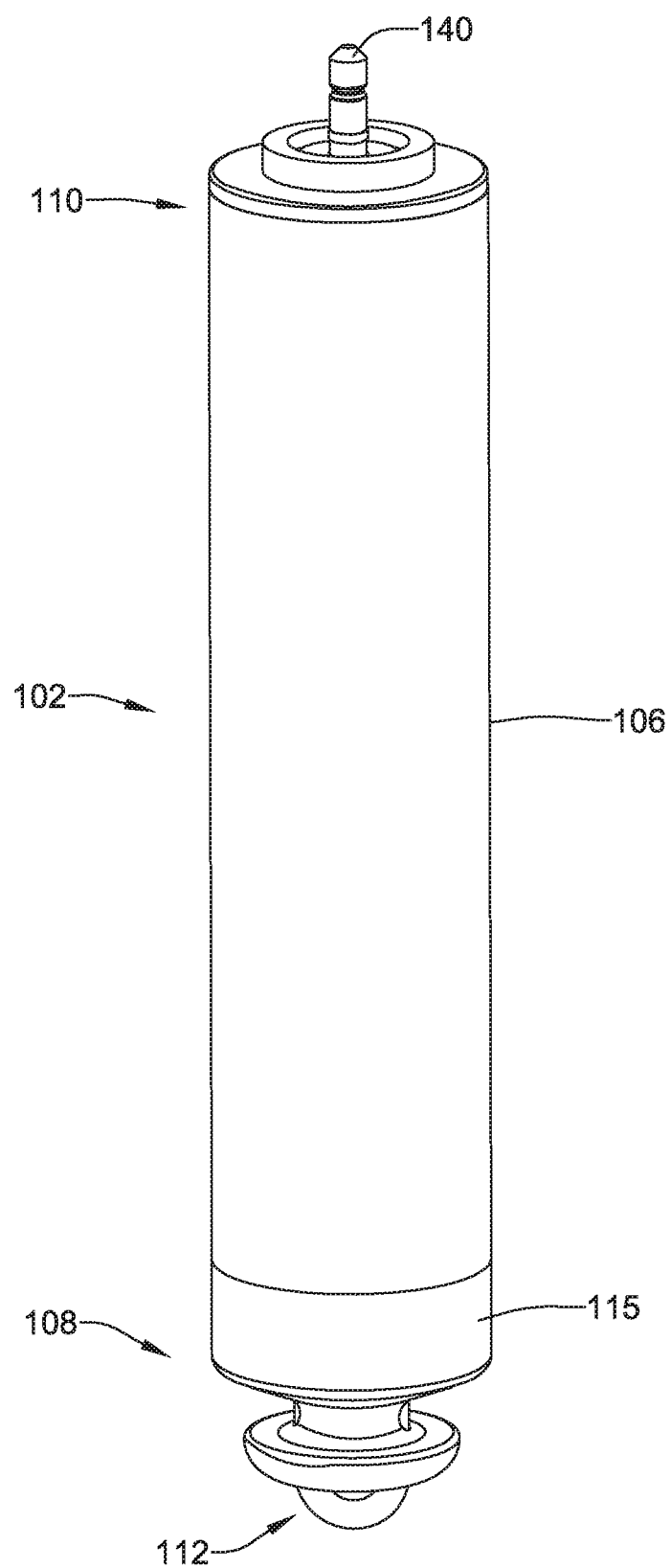
FIG. 9 is a side view of a device module forming a portion of the LCP of FIG. 8.
Figure 10:
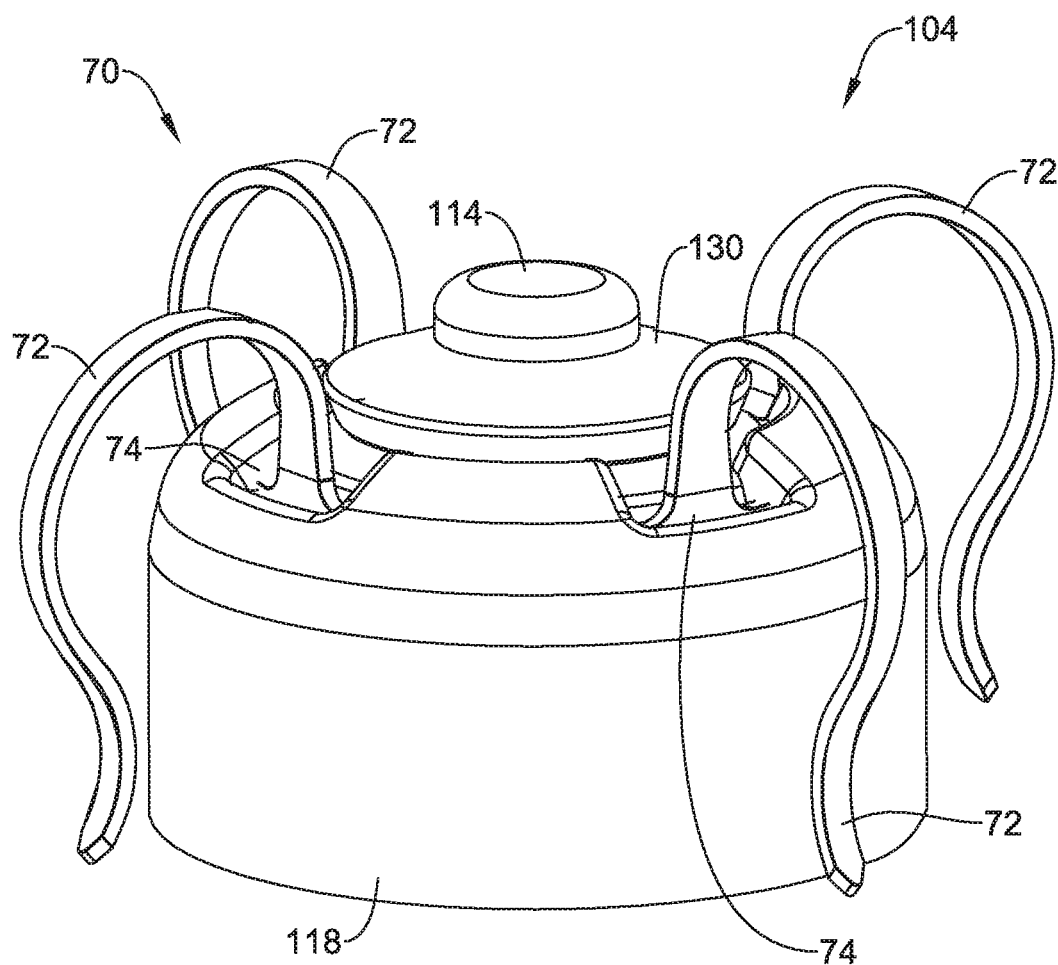
FIG. 10 is a perspective view of a fixation module forming a portion of the LCP of FIG. 8.
Figure 16:
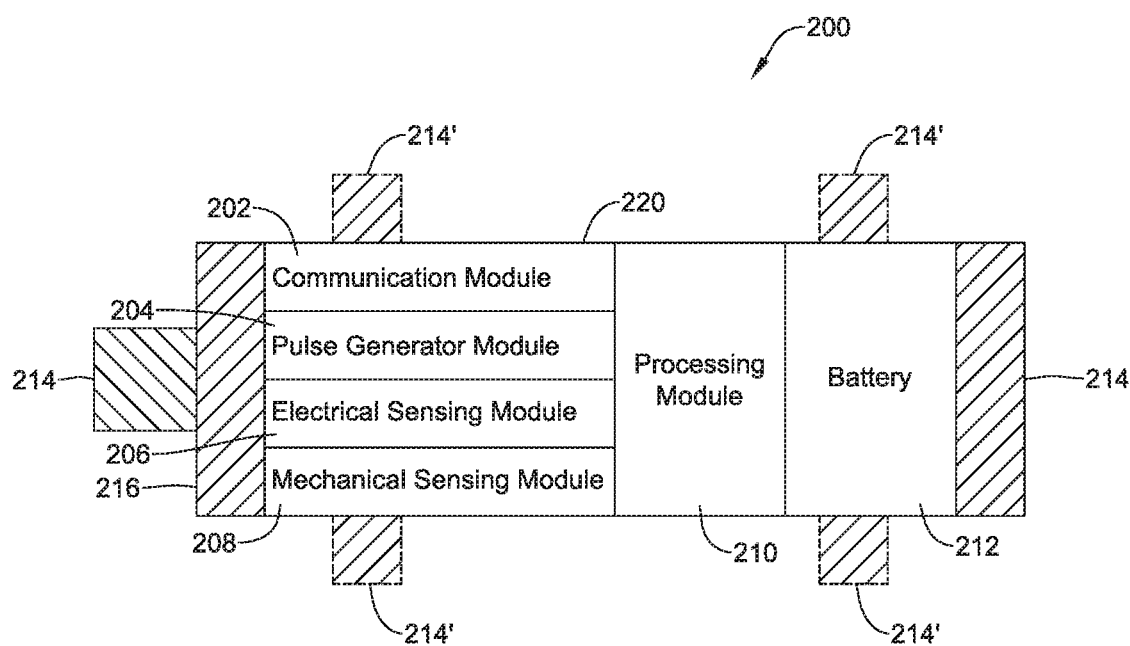
FIG. 16 is a schematic block diagram of an illustrative LCP in accordance with an example of the disclosure.

FIG. 16 is a schematic block diagram of an illustrative LCP in accordance with an example of the disclosure. The illustrative LCP may be implanted into a patient and may operate to deliver appropriate therapy to the heart, such as to deliver anti-tachycardia pacing (ATP) therapy, cardiac resynchronization therapy (CRT), bradycardia therapy, and/or the like. As can be seen in FIG. 16, the illustrative LCP 200 may be a compact device with all components housed within or directly on a housing 220. In some cases, the LCP 200 may be considered as being an example of the IMD 10 (FIG. 1), the IMD 50 (FIG. 2) or the IMD 100 (FIG. 8). In some instances, the LCP 200 may include one or more of a communication module 202, a pulse generator module 204, an electrical sensing module 206, a mechanical sensing module 208, a processing module 210, an energy storage module 212 (e.g., a battery), and electrodes 214.

As depicted in FIG. 16, the LCP 200 may include electrodes 214, which can be secured relative to the housing 220 and electrically exposed to tissue and/or blood surrounding the LCP 200. The electrodes 214 may generally conduct electrical signals to and from the LCP 200 and the surrounding tissue and/or blood. Such electrical signals can include communication signals, electrical stimulation pulses, and intrinsic cardiac electrical signals, to name a few. Intrinsic cardiac electrical signals may include electrical signals generated by the heart and may be represented by an electrocardiogram (ECG).

The electrodes 214 may include one or more biocompatible conductive materials such as various metals or alloys that are known to be safe for implantation within a human body. In some instances, the electrodes 214 may be generally disposed on either end of the LCP 200 and may be in electrical communication with one or more of the modules 202, 204, 206, 208, and 210. In embodiments where the electrodes 214 are secured directly to the housing 220, an insulative material may electrically isolate the electrodes 214 from adjacent electrodes, the housing 220, and/or other parts of the LCP 200. In some instances, some or all of the electrodes 214 may be spaced from the housing 220 and may be connected to the housing 220 and/or other components of the LCP 200 through connecting wires. In such instances, the electrodes 214 may be placed on a tail (not shown) that extends out away from the housing 220. As shown in FIG. 16, in some embodiments, the LCP 200 may include electrodes 214'. The electrodes 214' may be in addition to the electrodes 214, or may replace one or more of the electrodes 214. The electrodes 214' may be similar to the electrodes 214 except that the electrodes 214' are disposed on the sides of the LCP 200. In some cases, the electrodes 214' may increase the number of electrodes by which the LCP 200 may deliver communication signals and/or electrical stimulation pulses, and/or may sense intrinsic cardiac electrical signals, communication signals, and/or electrical stimulation pulses.

The electrodes 214 and/or 214' may assume any of a variety of sizes and/or shapes, and may be spaced at any of a variety of spacings. For example, the electrodes 214 may have an outer diameter of two to twenty millimeters (mm). In other embodiments, the electrodes 214 and/or 214' may have a diameter of two, three, five, seven millimeters (mm), or any other suitable diameter, dimension and/or shape. Example lengths for the electrodes 214 and/or 214' may include, for example, one, three, five, ten millimeters (mm), or any other suitable length. As used herein, the length is a dimension of the electrodes 214 and/or 214' that extends away from the outer surface of the housing 220. In some instances, at least some of the electrodes 214 and/or 214' may be spaced from one another by a distance of twenty, thirty, forty, fifty millimeters (mm), or any other suitable spacing. The electrodes 214 and/or 214' of a single device may have different sizes with respect to each other, and the spacing and/or lengths of the electrodes on the device may or may not be uniform.

In the embodiment shown, the communication module 202 may be electrically coupled to two or more of the electrodes 214, 214' and may be configured to deliver communication pulses to tissues of the patient for communicating with other devices such as sensors, programmers, other medical devices, and/or the like. Communication signals, as used herein, may be any modulated signal that conveys information to another device, either by itself or in conjunction with one or more other modulated signals. In some embodiments, communication signals may be limited to sub-threshold signals that do not result in capture of the heart yet still convey information. The communication signals may be delivered to another device that is located either external or internal to the patient's body. In some instances, the communication may take the form of distinct communication pulses separated by various amounts of time. In some of these cases, the timing between successive pulses may convey information. The communication module 202 may additionally be configured to sense for communication signals delivered by other devices, which may be located external or internal to the patient's body.

The communication module 202 may communicate to help accomplish one or more desired functions. Some example functions include delivering sensed data, using communicated data for determining occurrences of events such as arrhythmias, coordinating delivery of electrical stimulation therapy, and/or other functions. In some cases, the LCP 200 may use communication signals to communicate raw information, processed information, messages and/or commands, and/or other data. Raw information may include information such as sensed electrical signals (e.g. a sensed ECG), signals gathered from coupled sensors, and the like. In some embodiments, the processed information may include signals that have been filtered using one or more signal processing techniques. Processed information may also include parameters and/or events that are determined by the LCP 200 and/or another device, such as a determined heart rate, timing of determined heartbeats, timing of other determined events, determinations of threshold crossings, expirations of monitored time periods, accelerometer signals, activity level parameters, blood-oxygen parameters, blood pressure parameters, heart sound parameters, and the like. In some cases, processed information may, for example, be provided by a chemical sensor or an optically interfaced sensor. Messages and/or commands may include instructions or the like directing another device to take action, notifications of imminent actions of the sending device, requests for reading from the receiving device, requests for writing data to the receiving device, information messages, and/or other messages commands.

In at least some embodiments, the communication module 202 (or the LCP 200) may further include switching circuitry to selectively connect one or more of the electrodes 214, 214' and/or 214" to the communication module 202 in order to select which of the electrodes 214, 214' and/or 214" that the communication module 202 delivers communication pulses with. It is contemplated that the communication module 202 may be communicating with other devices via conducted signals, radio frequency (RF) signals, optical signals, acoustic signals, inductive coupling, and/or any other suitable communication methodology. Where the communication module 202 generates electrical communication signals, the communication module 202 may include one or more capacitor elements and/or other charge storage devices to aid in generating and delivering communication signals. In the embodiment shown, the communication module 202 may use energy stored in the energy storage module 212 to generate the communication signals. In at least some examples, the communication module 202 may include a switching circuit that is connected to the energy storage module 212 and, with the switching circuitry, may connect the energy storage module 212 to one or more of the electrodes 214/214'/214" to generate the communication signals.

As shown in FIG. 16, a pulse generator module 204 may be electrically connected to one or more of the electrodes 214, 214' and/or 214". The pulse generator module 204 may be configured to generate electrical stimulation pulses and deliver the electrical stimulation pulses to tissues of a patient via one or more of the electrodes 214, 214' and/or 214" in order to effectuate one or more electrical stimulation therapies. Electrical stimulation pulses as used herein are meant to encompass any electrical signals that may be delivered to tissue of a patient for purposes of treatment of any type of disease or abnormality. For example, when used to treat heart disease, the pulse generator module 204 may generate electrical stimulation pacing pulses for capturing the heart of the patient, i.e. causing the heart to contract in response to the delivered electrical stimulation pulse. In some of these cases, the LCP 200 may vary the rate at which the pulse generator module 204 generates the electrical stimulation pulses, for example in rate adaptive pacing. In other embodiments, the electrical stimulation pulses may include defibrillation/cardioversion pulses for shocking the heart out of fibrillation or into a normal heart rhythm. In yet other embodiments, the electrical stimulation pulses may include anti-tachycardia pacing (ATP) pulses. It should be understood that these are just some examples. The pulse generator module 204 may include one or more capacitor elements and/or other charge storage devices to aid in generating and delivering appropriate electrical stimulation pulses. In at least some embodiments, the pulse generator module 204 may use energy stored in the energy storage module 212 to generate the electrical stimulation pulses. In some particular embodiments, the pulse generator module 204 may include a switching circuit that is connected to the energy storage module 212 and may connect the energy storage module 212 to one or more of the electrodes 214/214'/214" to generate electrical stimulation pulses. In some cases, the pulse generator module 204 may provide pacing pulses to pace the RV of the heart H using electrode 214, and may provide pacing pulses to the LV of the heart H using electrode 214". In some cases, the pacing pulses generated for pacing the RV of the heart H by the pulse generator module 204 may be offset in time, have a different duration, have a different amplitude and/or have a different shape from the pacing pulses generated by the pulse generator module 204 for pacing the LV of the heart H, if desired.

The LCP 200 may further include an electrical sensing module 206 and a mechanical sensing module 208. The electrical sensing module 206 may be configured to sense intrinsic cardiac electrical signals conducted from the electrodes 214, 214' and/or 214" to the electrical sensing module 206. For example, the electrical sensing module 206 may be electrically connected to one or more of the electrodes 214, 214' and/or 214" and the electrical sensing module 206 may be configured to receive cardiac electrical signals conducted through the electrodes 214, 214' and/or 214" via a sensor amplifier or the like. In some embodiments, the cardiac electrical signals from electrodes 214 and/or 214' may represent local information from the RV, while the cardiac electrical signals from LV electrode 214" may represent local information from the LV of the heart H.

The mechanical sensing module 208 may include, or be electrically connected to, various sensors, such as accelerometers, including multi-axis accelerometers such as two- or three-axis accelerometers, gyroscopes, including multi-axis gyroscopes such as two- or three-axis gyroscopes, blood pressure sensors, heart sound sensors, piezoelectric sensors, blood-oxygen sensors, and/or other sensors which measure one or more physiological parameters of the heart and/or patient. Mechanical sensing module 208, when present, may gather signals from the sensors indicative of the various physiological parameters. The electrical sensing module 206 and the mechanical sensing module 208 may both be connected to the processing module 210 and may provide signals representative of the sensed cardiac electrical signals and/or physiological signals to the processing module 210. Although described with respect to FIG. 16 as separate sensing modules, in some embodiments, the electrical sensing module 206 and the mechanical sensing module 208 may be combined into a single module. In at least some examples, the LCP 200 may only include one of the electrical sensing module 206 and the mechanical sensing module 208. In some cases, any combination of the processing module 210, the electrical sensing module 206, the mechanical sensing module 208, the communication module 202, the pulse generator module 204 and/or the energy storage module may be considered a controller of the LCP 200.

The processing module 210 may be configured to direct the operation of the LCP 200 and may, in some embodiments, be termed a controller. For example, the processing module 210 may be configured to receive cardiac electrical signals from the electrical sensing module 206 and/or physiological signals from the mechanical sensing module 208. Based on the received signals, the processing module 210 may determine, for example, occurrences and types of arrhythmias and other determinations such as whether the LCP 200 has become dislodged. The processing module 210 may further receive information from the communication module 202. In some embodiments, the processing module 210 may additionally use such received information to determine occurrences and types of arrhythmias and/or and other determinations such as whether the LCP 200 has become dislodged. In still some additional embodiments, the LCP 200 may use the received information instead of the signals received from the electrical sensing module 206 and/or the mechanical sensing module 208—for instance if the received information is deemed to be more accurate than the signals received from the electrical sensing module 206 and/or the mechanical sensing module 208 or if the electrical sensing module 206 and/or the mechanical sensing module 208 have been disabled or omitted from the LCP 200.

After determining an occurrence of an arrhythmia, the processing module 210 may control the pulse generator module 204 to generate electrical stimulation pulses in accordance with one or more electrical stimulation therapies to treat the determined arrhythmia. For example, the processing module 210 may control the pulse generator module 204 to generate pacing pulses with varying parameters and in different sequences to effectuate one or more electrical stimulation therapies. As one example, in controlling the pulse generator module 204 to deliver bradycardia pacing therapy, the processing module 210 may control the pulse generator module 204 to deliver pacing pulses designed to capture the heart of the patient at a regular interval to help prevent the heart of a patient from falling below a predetermined threshold. In some cases, the rate of pacing may be increased with an increased activity level of the patient (e.g. rate adaptive pacing). For instance, the processing module 210 may monitor one or more physiological parameters of the patient which may indicate a need for an increased heart rate (e.g. due to increased metabolic demand). The processing module 210 may then increase the rate at which the pulse generator module 204 generates electrical stimulation pulses. Adjusting the rate of delivery of the electrical stimulation pulses based on the one or more physiological parameters may extend the battery life of the LCP 200 by only requiring higher rates of delivery of electrical stimulation pulses when the physiological parameters indicate there is a need for increased cardiac output. Additionally, adjusting the rate of delivery of the electrical stimulation pulses may increase a comfort level of the patient by more closely matching the rate of delivery of electrical stimulation pulses with the cardiac output need of the patient.

For ATP therapy, the processing module 210 may control the pulse generator module 204 to deliver pacing pulses at a rate faster than an intrinsic heart rate of a patient in attempt to force the heart to beat in response to the delivered pacing pulses rather than in response to intrinsic cardiac electrical signals. Once the heart is following the pacing pulses, the processing module 210 may control the pulse generator module 204 to reduce the rate of delivered pacing pulses down to a safer level. In CRT, the processing module 210 may control the pulse generator module 204 to deliver pacing pulses in coordination with another device to cause the heart to contract more efficiently. In cases where the pulse generator module 204 is capable of generating defibrillation and/or cardioversion pulses for defibrillation/cardioversion therapy, the processing module 210 may control the pulse generator module 204 to generate such defibrillation and/or cardioversion pulses. In some cases, the processing module 210 may control the pulse generator module 204 to generate electrical stimulation pulses to provide electrical stimulation therapies different than those examples described above.

Aside from controlling the pulse generator module 204 to generate different types of electrical stimulation pulses and in different sequences, in some embodiments, the processing module 210 may also control the pulse generator module 204 to generate the various electrical stimulation pulses with varying pulse parameters. For example, each electrical stimulation pulse may have a pulse width and a pulse amplitude. The processing module 210 may control the pulse generator module 204 to generate the various electrical stimulation pulses with specific pulse widths and pulse amplitudes. For example, the processing module 210 may cause the pulse generator module 204 to adjust the pulse width and/or the pulse amplitude of electrical stimulation pulses if the electrical stimulation pulses are not effectively capturing the heart (e.g. RV or LV capture). Such control of the specific parameters of the various electrical stimulation pulses may help the LCP 200 provide more effective delivery of electrical stimulation therapy.

In some embodiments, the processing module 210 may further control the communication module 202 to send information to other devices. For example, the processing module 210 may control the communication module 202 to generate one or more communication signals for communicating with other devices of a system of devices. For instance, the processing module 210 may control the communication module 202 to generate communication signals in particular pulse sequences, where the specific sequences convey different information. The communication module 202 may also receive communication signals for potential action by the processing module 210.

In further embodiments, the processing module 210 may control switching circuitry by which the communication module 202 and the pulse generator module 204 deliver communication signals and/or electrical stimulation pulses to tissue of the patient. As described above, both the communication module 202 and the pulse generator module 204 may include circuitry for connecting one or more of the electrodes 214, 214' and/or 214" to the communication module 202 and/or the pulse generator module 204 so those modules may deliver the communication signals and electrical stimulation pulses to tissue of the patient. The specific combination of one or more electrodes by which the communication module 202 and/or the pulse generator module 204 deliver communication signals and electrical stimulation pulses may influence the reception of communication signals and/or the effectiveness of electrical stimulation pulses. Although it was described that each of the communication module 202 and the pulse generator module 204 may include switching circuitry, in some embodiments, the LCP 200 may have a single switching module connected to the communication module 202, the pulse generator module 204, and the electrodes 214, 214' and/or 214". In such embodiments, processing module 210 may control the switching module to connect the modules 202/204 and the electrodes 214/214'/214" as appropriate. In some cases, the LV electrode 214" may also be coupled to the switching module and may be used for communication.

In some embodiments, the processing module 210 may include a pre-programmed chip, such as a very-large-scale integration (VLSI) chip or an application specific integrated circuit (ASIC). In such embodiments, the chip may be pre-programmed with control logic in order to control the operation of the LCP 200. By using a pre-programmed chip, the processing module 210 may use less power than other programmable circuits while able to maintain basic functionality, thereby potentially increasing the battery life of the LCP 200. In other instances, the processing module 210 may include a programmable microprocessor or the like. Such a programmable microprocessor may allow a user to adjust the control logic of the LCP 200 after manufacture, thereby allowing for greater flexibility of the LCP 200 than when using a pre-programmed chip. In still other embodiments, the processing module 210 may not be a single component. For example, the processing module 210 may include multiple components positioned at disparate locations within the LCP 200 in order to perform the various described functions. For example, certain functions may be performed in one component of the processing module 210, while other functions are performed in a separate component of the processing module 210.

The processing module 210, in additional embodiments, may include a memory circuit and the processing module 210 may store information on and read information from the memory circuit. In other embodiments, the LCP 200 may include a separate memory circuit (not shown) that is in communication with the processing module 210, such that the processing module 210 may read and write information to and from the separate memory circuit. The memory circuit, whether part of the processing module 210 or separate from the processing module 210, may be volatile memory, non-volatile memory, or a combination of volatile memory and non-volatile memory.

The energy storage module 212 may provide a power source to the LCP 200 for its operations. In some embodiments, the energy storage module 212 may be a non-rechargeable lithium-based battery. In other embodiments, the non-rechargeable battery may be made from other suitable materials. In some embodiments, the energy storage module 212 may be considered to be a rechargeable power supply, such as but not limited to, a rechargeable battery. In still other embodiments, the energy storage module 212 may include other types of energy storage devices such as capacitors or super capacitors. In some cases, as will be discussed, the energy storage module 212 may include a rechargeable primary battery and a non-rechargeable secondary battery. In some cases, the primary battery and the second battery, if present, may both be rechargeable.

To implant the LCP 200 inside a patient's body, an operator (e.g., a physician, clinician, etc.), may fix the LCP 200 to the cardiac tissue of the patient's heart. To facilitate fixation, the LCP 200 may include one or more anchors 216. The one or more anchors 216 may include any number of fixation or anchoring mechanisms. For example, one or more anchors 216 may include one or more pins, staples, threads, screws, helix, tines, and/or the like. In some embodiments, although not shown, one or more anchors 216 may include threads on its external surface that may run along at least a partial length of an anchor member. The threads may provide friction between the cardiac tissue and the anchor to help fix the anchor member within the cardiac tissue. In some cases, the one or more anchors 216 may include an anchor member that has a cork-screw shape that can be screwed into the cardiac tissue. In other embodiments, the anchor 216 may include other structures such as barbs, spikes, or the like to facilitate engagement with the surrounding cardiac tissue.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments.

What is claimed is:

1. An implantable medical device (IMD) comprising:
a device module having a proximal end and a distal end, the device module comprising:
a power source;
a controller operably coupled to the power source, the controller configured to sense cardiac electrical activity via two or more electrodes and deliver pacing pulses via two or more electrodes;
a first part of a releasable connector;
a fixation module comprising:
a plurality of fixation for anchoring the fixation module to the patient's heart;
a second part of the releasable connector, wherein the first part of the releasable connector and the second part of the releasable connector cooperate to releasably connect the device module with the fixation module; and
the device module having one or more first fluoroscopic markers and the fixation module having one or more second fluoroscopic markers, wherein the one or more first fluoroscopic markers and the one or more second fluoroscopic markers are arranged so that a predefined rotational alignment between one or more of the first fluoroscopic markers and one or more of the second fluoroscopic markers confirms that the releasable connector is in a fully connected state.

2. The IMD of claim 1, wherein the device module further comprises a proximal electrode and a distal electrode each operatively coupled to the controller, wherein the distal electrode is disposed on an elongated post extending distally from the first part of the releasable connector, and wherein the fixation module defines an aperture through which the elongated post extends to support the distal electrode on a distal side of the fixation module when the releasable connector is in the fully connected state.

3. The IMD of claim 1, wherein the device module further comprises a proximal electrode and a distal terminal each operatively coupled to the controller, and wherein the fixation module comprises a distal electrode on a distal side of the fixation module, and wherein the distal terminal of the device module is operatively coupled to the distal electrode of the fixation module when the releasable connector is in the fully connected state.

4. The IMD of claim 1, wherein the releasable connector comprises:
one or more locking tabs;
one more locking slots;
wherein the one or more locking tabs are configured to be moved into the one or more locking slots against a bias mechanism, after which the one or more locking tabs are configured to be rotated relative to the one or more locking slots until one or more of the locking tabs are pushed into one or more retaining recesses by the bias mechanism, at which time the releasable connector is in the fully connected state.

5. The IMD of claim 4, wherein at least one of the locking tabs and a location of at least one of the retaining recesses are marked by a corresponding one or more of the first fluoroscopic markers and/or one or more of the second fluoroscopic markers.

6. The IMD of claim 4, wherein the bias mechanism comprises a silicon spring seal situated between the device module and the fixation module.

7. The IMD of claim 1, wherein the releasable connector comprises:
one or more receivers;
one or more catches that are biased to extend into and catch one or more of the receivers to form an interference connection when the releasable connector is in the fully connected state.

8. The IMD of claim 7, wherein the first part of a releasable connector includes the one or more receivers and the second part of a releasable connector includes the one or more catches.

9. The IMD of claim 7, wherein the releasable connector further comprises a seal for sealing the one or more receivers and the one or more catches from an external environment when the releasable connector is in the fully connected state.

10. The IMD of claim 7, wherein the releasable connector further comprises one or more electrical contacts for making an electrical connection between the first part of a releasable connector and the second part of a releasable connector.

11. An implantable leadless cardiac pacemaker (LCP) configured to pace a patient's heart from a position within a cardiac chamber, the LCP comprising:
a fixation module configured for engagement with the cardiac chamber and a device module that is releasably securable to the fixation module for deployment within the cardiac chamber;
the fixation module comprising:
a fixation module housing;
a plurality of locking slots;
one or more retaining recesses;
an aperture configured to accommodate an electrode carried by the device module;
one or more fixation module fluoroscopic markers each marking a corresponding one of the plurality of locking slots or one or more retaining recesses of the fixation module;
the device module comprising:
a device module housing;
a plurality of locking tabs that are configured to cooperate with the locking slots of the fixation module to releasably secure the device module to the fixation module by inserting the plurality of locking tabs into the locking slots against a bias mechanism, and then rotating the device module relative to the fixation module until one or more of the locking tabs are pushed into one or more of the retaining recesses of the fixation module by the bias mechanism;
one or more device module fluoroscopic markers each marking a corresponding one of the plurality of locking tabs of the device module;
wherein the one or more device module fluoroscopic markers are arranged relative to the one or more fixation module fluoroscopic markers so that a predefined alignment between one or more of the fixation module fluoroscopic markers and one or more of the device module fluoroscopic markers at least partially confirms that the device module is fully secured to the fixation module;
a power source disposed within the device module housing;
a first electrode disposed on the device module housing and a second electrode disposed on an elongated post extending distally of the plurality of locking tabs, the elongated post configured to extend through the aperture in the fixation module housing to place the second electrode in a position where the second electrode can contact cardiac tissue when the device module is engaged with the fixation module and the LCP is implanted; and a controller disposed within the device module housing and operably coupled to the power source, the controller configured to sense cardiac electrical activity and to deliver pacing pulses via one or more of the first electrode and the second electrode.

12. The LCP of claim 11, wherein the fixation module further comprises a plurality of fixation tines that are configured to extend distally into the patient's cardiac tissue and then back proximally to hook the patient's cardiac tissue to thereby anchor the fixation module to the patient's heart.

13. The LCP of claim 11, wherein the bias mechanism comprises a resilient seal that is configured to engage corresponding mating surface on the fixation module housing and the device module housing.

14. The LCP of claim 11, wherein one or more of the locking tabs of the device module include one or more of the device module fluoroscopic markers, and wherein the fixation module comprises one or more of the fixation module fluoroscopic markers secured relative to the fixation module housing, the one or more fixation module fluoroscopic markers are configured to indicate a relative rotational orientation of the fixation module relative to the locking tabs of the device module under fluoroscopy.

15. An implantable leadless cardiac pacemaker (LCP) configured to pace a patient's heart from a position within a cardiac chamber, the LCP comprising:

a fixation module configured for engagement with the cardiac chamber and a device module that is releasably securable to the fixation module for deployment within the cardiac chamber;

the device module comprising:
a device module housing;
an elongated post extending distally from the device module housing, the elongated post comprising one or more receivers and one or more electrical contacts disposed on a side of the elongated post;

the fixation module comprising:
a fixation module housing;
one or more electrodes on a distal side of the fixation module housing;
a post receiving aperture for receiving the elongated post of the device module;
one or more catches that are biased to extend into and catch one or more of the receivers of the elongated post when the elongated post is received by the post receiving aperture; and
one or more electrical contacts for making an electrical connection with one or more of the electrical contacts on the side of the elongated post when the elongated post is received by the post receiving aperture, wherein one or more of the electrical contacts of the fixation module are operatively coupled to one or more of the electrodes on the distal side of the fixation module housing; and
one or more fluoroscopic markers for indicating if the elongated post is sufficiently received by the post receiving aperture to be in a fully connected state.

16. The LCP of claim 15, further comprising a seal for providing a seal between the elongated post of the device module and the fixation module for sealing the one or more electrical contacts of the fixation module from an external environment when the elongated post is received by the post receiving aperture.

17. The LCP of claim 15, wherein the one or more receivers comprise one or more grooves formed in an outer surface of the elongated post.

18. The LCP of claim 17, wherein the one or more catches comprise a coil spring that is biased to extend into and catch one or more of the grooves of the elongated post.

19. The LCP of claim 17, wherein the one or more catches comprise a leaf spring that is biased to extend into and catch one or more of the grooves of the elongated post.

* * * * *